(12) United States Patent
Osborn

(10) Patent No.: US 9,728,101 B2
(45) Date of Patent: Aug. 8, 2017

(54) SYSTEM AND METHOD FOR ASSESSING AND IMPROVING A USER'S LIFE SKILLS AND SELF-EFFICACY FOR LIFE STAGE READINESS

(71) Applicant: Sheri Kemp Osborn, Austin, TX (US)

(72) Inventor: Sheri Kemp Osborn, Austin, TX (US)

(*) Notice: Subject to any disclaimer, the term of this patent is extended or adjusted under 35 U.S.C. 154(b) by 99 days.

(21) Appl. No.: 13/871,950

(22) Filed: Apr. 26, 2013

(65) Prior Publication Data

US 2014/0065585 A1 Mar. 6, 2014

Related U.S. Application Data

(60) Provisional application No. 61/696,255, filed on Sep. 3, 2012.

(51) Int. Cl.
*G09B 19/00* (2006.01)
(52) U.S. Cl.
CPC .................................. *G09B 19/00* (2013.01)
(58) Field of Classification Search
USPC ................................................. 434/236, 238
See application file for complete search history.

(56) References Cited

U.S. PATENT DOCUMENTS 6,186,145 B1* 2/2001 Brown .......................... 128/897
6,497,577 B2* 12/2002 Kanter .......................... 434/236

* cited by examiner

*Primary Examiner* — Kesha Frisby
(74) *Attorney, Agent, or Firm* — Jerry M. Keys; Matheson Keys Daffer & Kordzik PLLC

(57) ABSTRACT

A computer-implemented mental and emotional life efficacy development system and method are disclosed which assist lay individuals to measure and improve their mental health and emotional capabilities and life skill deficits to increase the individual's ability to achieve life efficacy. A scoring subsystem measures competencies or deficits in a breadth of critical life skills. The system provides feedback concerning personality traits and mental and emotional deficits and compares the user's scores to the scores of those who are successfully navigating a particular life step. This pinpoints deficits for which the user can receive training and treatment tailored to that user's personality and individual difficulties. Through the collection and aggregating of such symptoms, a preliminary diagnosis is made of the user's mental health and life skills. This diagnosis is subsequently refined before it is used to offer emotion and/or mental health care treatment and life skills training for life efficacy competency.

36 Claims, 21 Drawing Sheets

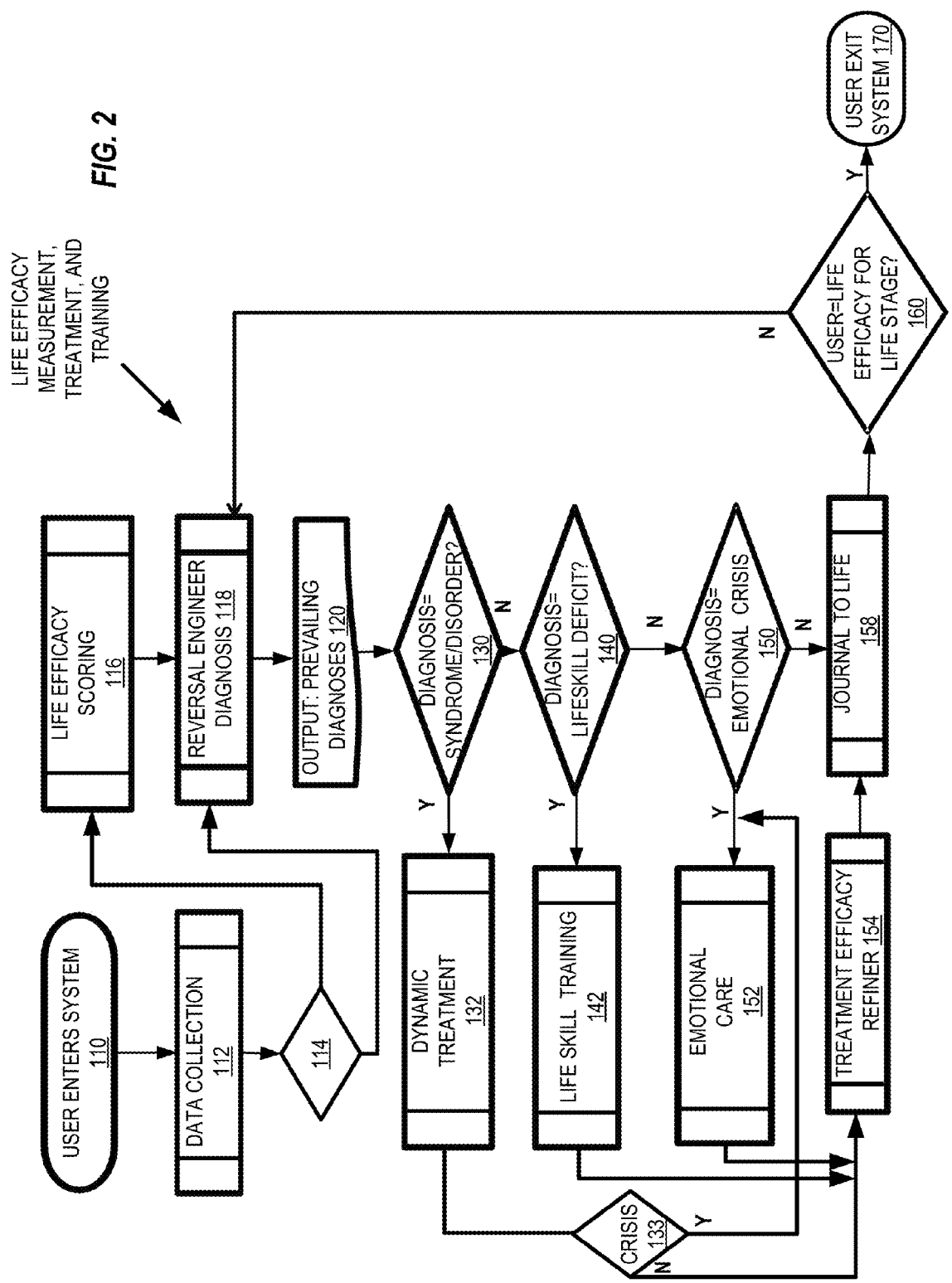

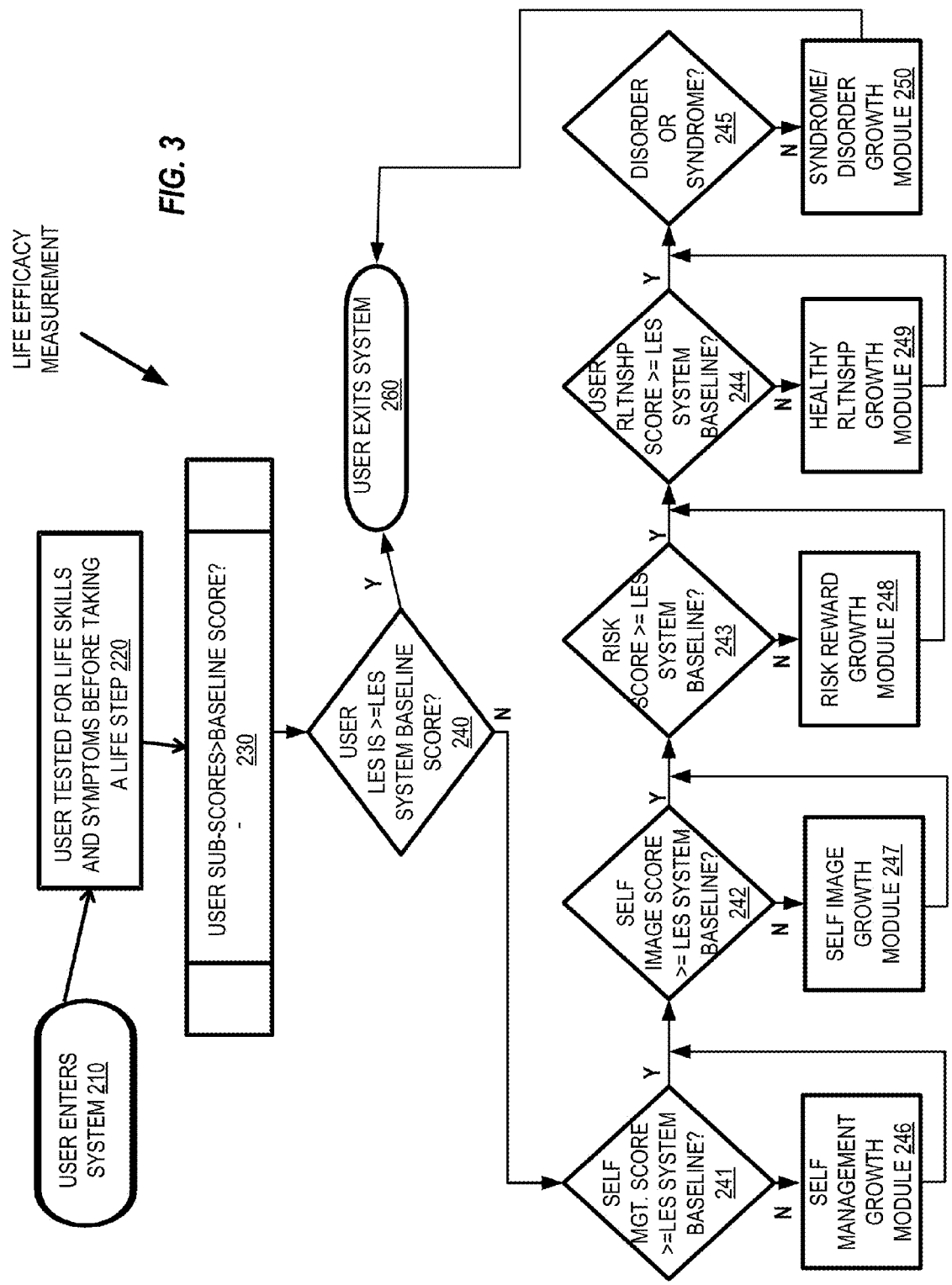

EXAMPLE PERSONALITY PROFILING DIALOG - APPLICATION 750.1

HOW DO YOU FEEL ABOUT......

YOU HAVE JUST BEEN INVITED TO GO OUT WITH JUST A FEW FRIENDS TO A PARTY . YOU....

750.11 ○ HATE THE IDEA
750.12 ○ AREN'T HAPPY WITH THE SUGGESTION BUT WILL GO ALONG
750.13 ○ DON'T HAVE A PREFERENCE
750.14 ○ MAY ENJOY THE EXPERIENCE
750.15 ○ LOVE THE IDEA

FIG. 14

A CHART 755 FOR USING PERSONALITY DEFINITION RESPONSES
TO SELECT A THERAPEUTIC METHODOLOGY

| FIELD NAME VALUE | PERSONALITY TRAITS ARE | STARTING THERAPY METHODOLOGY |
|---|---|---|
| NUM_INTERRELATE> 0 AND NUM_MOTIVATE> 0   755.1 | EXTROVERTED + PEOPLE / ACCEPTANCE | COGNITIVE BEHAVIOR 756.1 |
| NUM_INTERRELATE> 0 AND NUM_MOTIVATE <= 0   755.2 | EXTROVERTED + DATA / GOAL | POSITIVE PSYCHOLOGY 756.2 |
| NUM_INTERRELATE <= 0 AND NUM_MOTIVATE> 0   755.3 | INTROVERTED +PEOPLE /ACCEPTANCE | PSYCHOANALYSIS 756.3 |
| NUM_INTERRELATE <= 0 AND NUM_MOTIVATE <= 0   755.4 | INTROVERTED = DATA / GOAL | OPERANT CONDITIONING 756.4 |

FIG. 15

VIRTUAL THERAPY TO CALENDAR SCREEN

GOALS 820

821
GOAL 1: _____
MILESTONE 1: _____
  TASK 1: _____
  TASK 2: _____
  TASK X: _____
MILESTONE 2: _____
MILESTONE X: _____

MILESTONES 822

REWARDS

822
TASK 1: _____
  DATE TO COMPLETE: __/__/__
823 — REWARD FOR COMPLETION: _____
824 — REMINDER TO CALENDAR ON: __/__/__

*FIG. 20*

SYSTEM AND METHOD FOR ASSESSING AND IMPROVING A USER'S LIFE SKILLS AND SELF-EFFICACY FOR LIFE STAGE READINESS

FIELD OF INVENTION

The present invention relates generally to systems, methods and computer program products for assessing and improving an individual user's life skills and self-efficacy for life stage readiness for a life stage transition, including helping the user with a variety of emotional and/or mental problems the user may have so that the user can better understand, manage, and/or treat such problems. More particularly, the systems, methods, and computer program products gather data of the user's symptoms and other evidence of the user's emotional and mental health that are useful in assessing, managing, and treating the user problems, provide tools to meaningfully measure emotional- and mentally-related life skill competencies and self-efficacy, guide the user to appropriate therapeutic treatment or training programs, and provide means to measure improvements in the user's life skill competencies and the user's readiness for a life stage transition, such as going to college or overcoming a chemical dependency.

BACKGROUND OF INVENTION

The damage to people and the cost of the limited reach of mental and emotional health care in America is staggering. One in four students leaves college prior to their junior year due to such problems, yet the SAT test confirms that these students have the scholastic aptitude to handle college-level coursework. Fifty percent of college students will either drop out before getting their degree or take much longer to complete their college education. Yet all of these young adults passed an entrance exam attesting to their intellectual capacity to perform the work.

Twenty-six million American workers have a chemical dependency problem yet after 40 years, the United States' war on drugs has cost $1 trillion and hundreds of thousands of lives. For what? Drug use is rampant and violence associated therewith is even more brutal and widespread.

Each year, Americans spend more than $90 billion on alcohol. The U.S. Department of Labor has estimated that substance abuse costs American businesses more than $100 billion/year. The divorce rate in America for first marriage is 41%; 60% for second marriages, and 73% for a third marriage in America.

According to the U.S. Department of Health and Human Services, Health Resources and Services Administration, Maternal and Child Health Bureau, during 2007-2009, mental health services were needed, but not received, by about 11.3 million adults annually (on average), corresponding to 5 percent of adults in the United States. The reasons included: cost or lack of adequate insurance coverage (49.5%), a fear of stigma (21.8%), and lack of accessibility to services (14.8%).

In the past, there was no universal rating system to measure emotional and mental health capabilities for successfully taking a life step. Therapists or mental health care practitioners may be able to gauge a patient's readiness for college or marriage but the statistics point out that most people do not seek out these professionals until there is a life problem. Thus, there is a need for an easily accessible system and method to help users to identify mental and emotional deficits before the user's life is seriously impacted.

A need also exists for a more affordable and efficient system and method to bring affordable mental and emotional health care to anyone that has Internet access or a cell phone. There is also a need for a cost effective and efficient way to bring practical life skills training and emotional and mental health care knowledge currently residing in self-help books, tapes, and other physical media to any person via online methods. There is also a need for an interactive means of using such knowledge to teach and treat individuals with emotional and/or mental problems.

Additionally there is a need to provide training to such individuals in soft skills such as relationship skills, appropriate attitude towards risk/reward for the desired life stage or life goal, and self-management techniques so that individuals may learn to set goals for their lives, take concrete steps to meet those goals, and access a breadth of interactive therapeutic routines covering a variety of emotional and mental health and life skills needs that uses limited mental health jargon and speaks to the user as a friend or mentor would.

SUMMARY OF THE INVENTION

The present invention provides for systems, methods and computer program products for assessing and improving a user's life skills and self-efficacy for life stage readiness. The system, computer-implemented method, and computer program product collect from the user and store in a database user symptoms and other evidence of the user's emotional and mental health; assess the self-efficacy of the user's readiness to address a life stage transition based upon the collected user symptoms and other evidence; generate a plurality of potential differential diagnoses based upon the assessments; rank the plurality of potential diagnoses from most likely to least likely; select a first treatment program or a first training program for the first most likely diagnosis from a plurality of treatment and training programs stored in a database; using the selected first treatment program or first training program, interactively engage in at least one session with the user to improve the user's self-efficacy for life stage readiness; select a second treatment program or a selected training program from the plurality of treatment and training programs for the second most likely diagnosis; using the selected second treatment program or second training program, interactively engage in at least one session with the user to improve the user's self-efficacy for life stage readiness; guide the user to input a value rating of the sessions of each of the plurality of treatment programs or training programs taken by the user; and in response to the user's ratings of the sessions of the treatment or training programs taken, determine the user's most likely diagnosis from the plurality of differential diagnoses. The system, computer-implemented method, and computer program product may further make suggestions to the user to improve his or her life efficacy competencies for a particular life stage transition.

To assess the self-efficacy of the user's readiness to address a life stage transition in a particular embodiment, the system, computer-implemented method and computer program product engage in at least one interactive session with the user, measure a plurality of life skill competencies, wherein the measuring may include developing scores of the user's self-image, self-management skills, risk/reward predisposition, interpersonal skills, and existence or non-existence of one or more syndromes/disorders, comparing the user's scores for each of the life skill competencies assessed to a baseline score for each of the plurality of life skill competencies measured which is predictive of success, determining whether the user has a deficit score in any of the plurality of measured life skill competencies; and determining a composite score of the measured life skill competencies scores and comparing the composite score to a baseline composite score which is predictive of readiness for success in a life stage transition to determine if the user is ready for successfully transitioning a particular life stage.

In another particular embodiment, the system, method and computer product heuristically determine a composite score from the plurality of scores for the plurality of measured life skill competencies.

BRIEF DESCRIPTION OF DRAWINGS

For a more complete understanding of the present invention, and the advantages thereof, reference is now made to the following descriptions taken in conjunction with the accompanying drawings, in which:

FIG. 2 is a top-level flow diagram of an exemplary method carried out by the system of FIG. 1b. It details the process that a user experiences and follows, including which modules are used and the order in which the modules operate.

FIG. 3 is a flow diagram of an exemplary method for carrying out the Life Efficacy Scoring ("LES") methodology used by the system of FIG. 1b. Each LES subscore helps the user understand which of their mental, emotional, or life skill capabilities need improvement.

FIG. 14 is a personality refining data entry screen that solicits a user's preferences within the context of various social, business and familial settings to clarify the user's personality traits.

FIG. 15 is a chart detailing now a user's personality traits guide the system to decide which school of therapy the system offers the user as they are treated for a mental or emotional problem or syndrome.

FIG. 20 is an example of the data entry screen the user may see to take the goals he or she set as part of his or her therapy session and gives each life changing step a date and various reminders so the user will make life changing steps a meaningful part of the user's day to day activities.

Corresponding reference characters in the drawings indicate corresponding parts throughout the drawings.

DETAILED DESCRIPTION OF ILLUSTRATIVE EMBODIMENTS

The principles of the present invention and their advantages are best understood by referring to FIGS. 1-20.

In the following detailed description of illustrative or exemplary embodiments of the disclosure, specific embodiments in which the disclosure may be practiced are described in sufficient detail to enable those skilled in the art to practice the disclosed embodiments. For example, specific details such as specific method steps, structures, elements, and connections are presented herein. However, it is to be understood that the specific details presented need not be utilized to practice the embodiments of the present disclosure. It is also to be understood that other embodiments may be utilized and that logical, architectural, programmatic, mechanical, electrical and other changes may be made without departing from the general scope of the disclosure. The following detailed description is, therefore, not to be taken in a limiting sense, and the scope of the present disclosure is defined by the appended claims and equivalents thereof.

References within the specification to "one embodiment," "an embodiment," "embodiments," or "one or more embodiments" are intended to indicate that a particular feature, structure, or characteristic described in connection with the embodiment is included in at least one embodiment of the present disclosure. The appearance of such phrases in various places within the specification are not necessarily all referring to the same embodiment, nor are separate or alternative embodiments mutually exclusive of other embodiments. Further, various features are described which may be exhibited by some embodiments and not by others. Similarly, various requirements are described which may be requirements for some embodiments but not other embodiments.

Figure 1A:
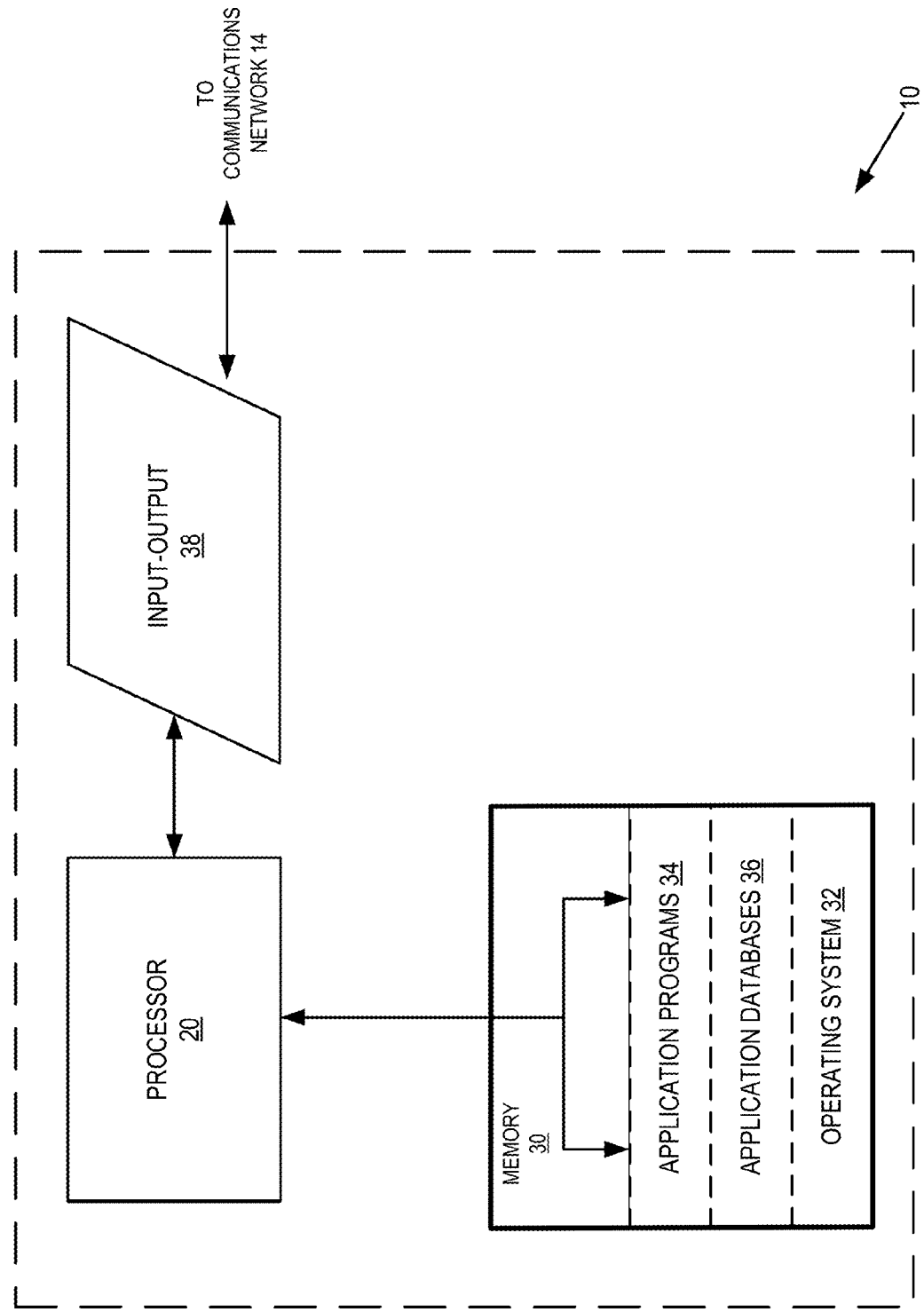
FIG. 1a is a block diagram illustration of an exemplary computer system within which various aspects of the disclosure can be implemented, according to one or more embodiments.

With reference now to the figures, wherein like reference numbers denote like parts, FIG. 1a illustrates a typical hardware configuration of a computer processing system 10 which is representative of a hardware environment for practicing the present invention. Referring to FIG. 1a, computer system 10 may have a processor 20 coupled to various other components. A computer operating system 32 may run on processor 20 and control and coordinate the functions of the various components of FIG. 1a. Application programs 34 stored in memory 20 and coupled to various application databases 36 may run in conjunction with operating system 32 and provide calls to operating system 32 where the calls implement the various functions or services to be performed by application programs 34. Applications may be further broken down into program modules. Application programs 34 include, for example, an application for assessing and improving an individual user's life skills or self-efficacy to increase the user's ability to transition a life event, as described in more detail below in association with FIG. 1b. It should be noted that software components including operating system 32 and the application programs 34 of the present invention may be loaded into the processing system's main memory 30 for execution.

Emotional and mental health problems are difficult to treat and require cooperation and perseverance from a person who is calm and open to change. Many aspects of the current system of mental health care requires the patient to place their emotional and mental stability in the hands of a stranger, at a time that is typically inconvenient to them in an unfamiliar place for the amount of time they can afford or the insurance company approves them to have. The systems and methods of the present invention provide both an alternative and a supplement to this traditional approach.

The methods implemented by the system guide the users to present evidence of their life skills, emotional and mental health symptoms and personality characteristics to the system in laymen's terms, which in turn provides immediate feedback in the form of i) a life efficacy score for assessing the readiness of the users to successfully undertake a life stage transition and/or ii) ranked potential diagnoses of mental and/or emotional problems. The system also suggests treatment to treat any identified disorders and syndromes or training to improve any identified deficit life skills. The system may also direct the user to a program module that guides the users through an emotion care process to reduce any negative user emotions, such as depression, anger, or discouragement, caused by a treatment. The system provides such measurement, diagnosis, treatment, and training capabilities in an engaging and fun environment that lead the users to enjoyable emotional growth. The resulting positive environment, in turn, increases a user's treatment frequency and so improves the user's overall recovery and healing.

Figure 1B:
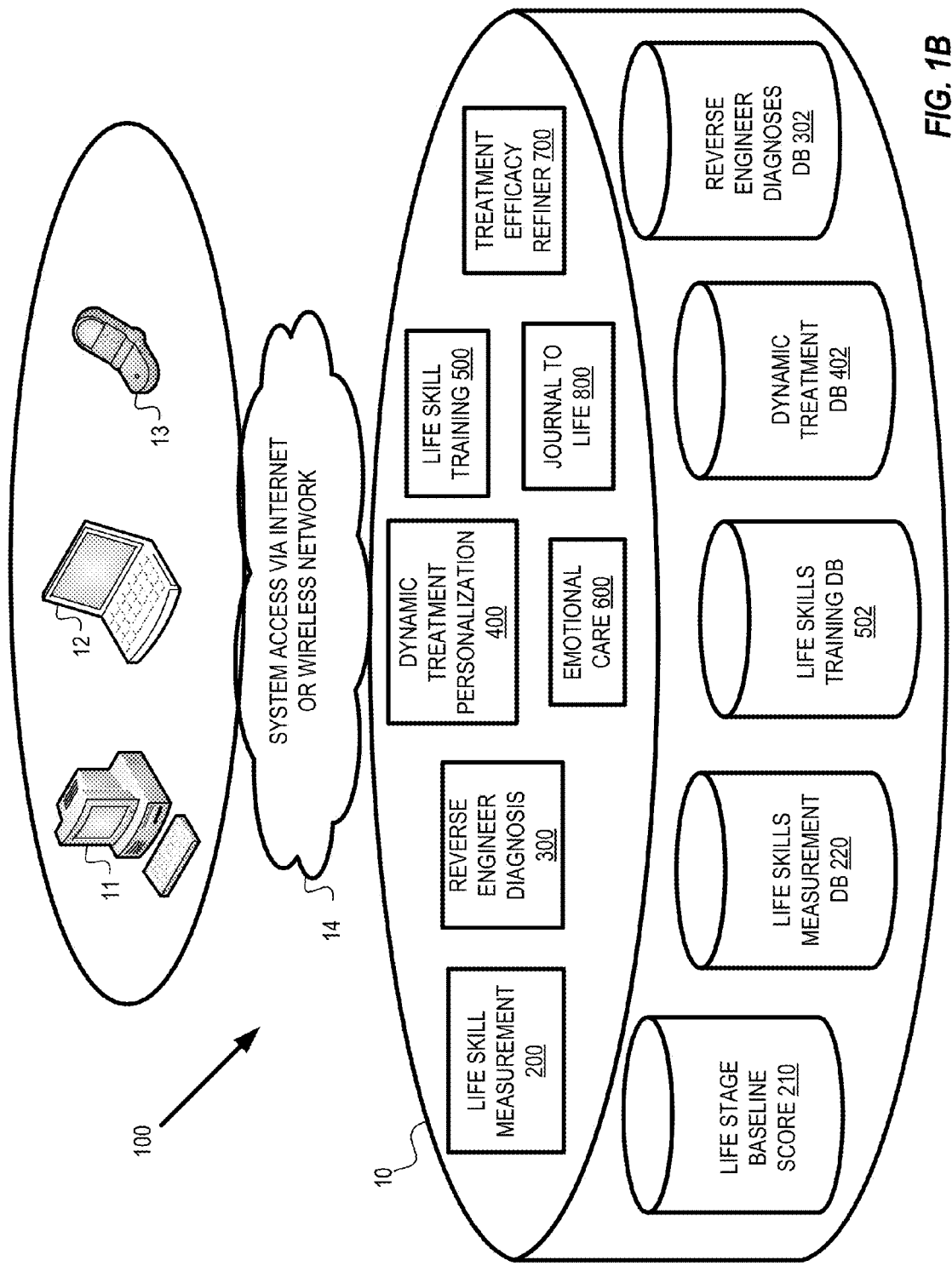
FIG. 1b is a diagram of the computer-implemented system for assessing and improving a user's life skill and self-efficacy for life stage readiness, illustrating the variety of user inputs through typical communication networks and the top-level application program modules and database modules for implementing the various aspects of the disclosure.

FIG. 1b depicts an illustrative embodiment of a networked system 100 for implementing the self-guided methods of assessing and improving an individual user's life skills or self-efficacy to increase the user's ability to transition a life event. Self efficacy is herein defined as a person's belief in his or her ability to complete a future task or solve a future problem. It is a term coined by Albert Bandura in the 1970s to identify his theory that the beliefs a person has about his or her abilities affect their actual outcomes. The self-guided system 100 also helps users to diagnose, understand and treatment their current emotional and mental problems. Thus, the system 100 provides a mental health and emotion care solution that a user can use in the privacy of their home or office when they desire it, at their own pace. The system and methods thus permit the users to take responsibility for their emotional and mental health. The system 100, however, may also be used in connection with traditional treatment by a counselor.

A user seeking help may access the computer processing system 10 (also referred to herein as a "computer system" or "computer server") of the networked system 100 to run application programs coupled to multiple databases, which stores various information, as hereinafter described. The users may access the computer system 10 from a variety of user access devices 11, 12, and/or 13 over a local area network or a conventional external telecommunications link 14, such as the Internet or a wireless cellular network. FIGS. 1a and 1b may include additional components that are not depicted for ease of understanding.

The system 100 includes a life skills measurement program module 200 that can be interactively accessed by the user through conventional user interfaces so that the system 100 can collect user symptoms and other evidence of the user's emotional and mental health, life skills and personality. The collected data needed for a user life efficacy assessment may be stored in a life skills measurement database 220. The life skills measurement module 200 may then be used to assess the self-efficacy of the user's readiness to address a life stage transition by scoring certain life skill competencies based upon the collected user symptoms and other evidence of the user's life skills, emotional and mental health, and personality and then comparing the resulting user's scores with life skill baseline scores stored in a life stage baseline score database 210 that reflect baseline scores for various life skills that are predictive of success.

The system 100 further includes a reverse engineering diagnosis program module 300. The module is programmed to implement a differential diagnostic procedure that generates a set of alternative probable candidate diagnoses for a given set of input conditions. The module uses this process to generate a variety of potential differential diagnoses, of which plurality of the most likely, five for example, are stored in a reverse engineering diagnoses database 302. The reverse engineering diagnosis module 300 also ranks the plurality of potential diagnoses from most likely to least likely. The system 100 then outputs suggestions to the user as to treatment for an identified diagnosis or training to improve his or her life skill competencies for a particular life stage transition.

The system also includes a dynamic treatment personalization program module 400 and associated database 402 containing treatment programs for treating various mental or emotional syndromes and disorders of a user and a life skills training program module 500 and associated database 502 of training programs for providing various life skills training to a user with various life skill deficits identified by the user assessment made by the life skills measurement module 200.

The dynamic treatment program module 400 may also include a dynamic personalization program that uses collected information about the user's personality to adapt a selected treatment program to the user's personality.

The system 100 may also include an emotion care program module 600 that, based upon user responses to questions following a treatment session, assesses whether the user is having negative emotions such as depression, anger, or discouragement, as a result of treatment and then interactively engages with the user to cheer up, calm, or encourage the user.

The system 100 may further include a treatment efficacy refiner program module 700 that uses feedback for the user's experience with a selected treatment program to refine the selected treatment program for use by the user in future sessions, thereby dynamically customizing the user's treatment to the user's individual needs and personality. The system further may include a Journal to Life program module 800 that includes capabilities for periodically outputting reminders of goals, tasks, and milestones to the user's access device, such as a personal digital assistant for example, to reinforce the steps to be taken by the user following a treatment session to improve or maintain the user's life skill competencies and self-efficacy for a particular life stage transition.

FIG. 2 is a high level flow diagram of an exemplary method that depicts the high-level steps of how the system 100 may interact with a user. In step 110, the user logs into the system 100 through the presenting user interface. In step 112, the user, in response to questions from life skill measurement program module 200 or reverse engineer diagnosis module 300 of the system, interactively collects data about the user's symptoms and other evidence of the user's life skills, emotional and mental health, and personality. At the user's option in step 114, the system in step 116 may output a composite life efficacy score and/or a set of individual life skill scores of certain life skill competencies based upon the collected data, as will be described in more detail hereinafter in connection with FIG. 3, or alternatively proceed directly to step 118.

In step 118, the reverse engineer diagnosis program module 300 converts the collected data relating to symptoms and other evidence of emotional and mental health into a variety of differential diagnoses which are initially ranked and then stored in database 302. In step 120, the module 300 determines whether the first ranked diagnosis is a syndrome or disorder. If "no", in step 130, the module 300 determines whether the first ranked diagnosis is a life skill deficit. If still "no", in step 150, the module determines if the user in an emotional crisis or otherwise has high negative emotions.

In step 130, if the determination is "yes", the system identifies the diagnosis as a syndrome or disorder, associates the identified syndrome or disorder with a particular treatment program in the dynamic treatment module database 402, and invites the user to enter into a treatment session 132 with the identified treatment program for that particular syndrome or disorder. At the end of treatment session 132, the user is invited to provide feedback regarding the user's emotional state.

If the determination in step 130 is "no" and the determination in step 140 is "yes", the system identifies the diagnosis as a deficit life skill and then invites the user to enter into a training session with a stored training program associated with improving the identified life skill.

If the determination in steps 130 and 140 are both "no" and the determination in step 150 is "yes", the system identifies the diagnosis as an emotional crises and then invites the user to engage in an emotional care session with the emotional care module 600. Software implemented algorithms may be used to further refine and prioritize the initial differential diagnoses identified in steps 130, 140, and 150. For example, a syndrome may be further refined to be a general anxiety or a PTSD diagnosis and a life skill deficit may be further refined to be a self-management skill deficiency.

In step 133, the system determines if the treatment session in step 132 caused the user to have negative emotions based upon input from the user in step 132. If yes, the user is invited to enter into a session with the emotion care module 600 to help the user cope with their negative emotions.

In step 154, based upon input from the user regarding the treatment or training session 132 or 142 in which he or she was most recently engaged and the user's collected personality traits and preferences, the treatment refiner module 700 refines the treatment program to make the user's experience with the next treatment session more enjoyable and more useful to the user.

In step 158, after each treatment session the user is directed to the Journal of Life module 800, which will coach the user to set some goals/milestones and to take positive steps in their life. Particularly, module 800 will instruct the user to set goals and milestones that make sense in their own world and make positive steps towards life improvement. In step 160, the user again provides feedback to the system 100 so that the life skill measurement module 200 can remeasure the user's life skill competencies and recompute the user's life-efficacy scores and life skill competencies to determine if the user is ready for a particular like stage transition and/or refine the prevailing diagnosis 120. If "yes", the user exits the system. If "no", the user is directed to repeat the steps in the method, and the system selects a treatment for the top ranked diagnosis. Alternatively, the user may choose to get more training on relationship skills (life skills) or choose to get more therapy for PTSD.

FIG. 3 is a more detailed flow diagram of an exemplary embodiment of the life skills measurement process or life efficacy scoring 116 implemented by life skills measurement module 200. In step 210, the user may enter the system and interactively engages with the life skill measurement module 200 before the user embarks upon a life stage to assess his or her readiness for successfully transitioning the life stage. In step 220, the module 200 interactively questions the user to collect data about the user's symptoms and other evidence of the user's life skills, emotional and mental health, and personality. In step 230, the module assesses a variety of like skills, such as for example self-image, self-management, risk/reward predisposition, interpersonal relationship skills, and the existence or non-existence of one or more syndromes or disorders by scoring each of the individual life skills tested and then generate a composite Life Efficacy Score ("LES"). In step 240, the user's composite LES score is then compared to a baseline composite LEC score. If the user's composite LES is greater than the composite LES baseline score, the user's self-efficacy and life skill competencies are sufficiently high that the user is ready for the life state transition being addressed, and the user exits the system in step 260. If the user's composite LES score is less than the composite baseline score, the program module 200 then compares the user's LES sub scores to a baseline score predictive of success for each of the selected tested life skills in steps 241, 242, 243, 244, 245, respectively. If the user's individual LES score is less than the baseline score for a selected life skill, the system guides the user to a training or treatment module that will either offer training in the deficit life skill or offer therapeutic treatment for the syndrome or disorder in steps 246, 247, 248, 249, 250, respectively. The user may continue using the system and repeating the process until the user's scores are above the composite LES baseline score in step 240, in which case the user exits the system in step 260.

In summary, the life skills measurement module 200 uses the LES scoring process as a means to quantitatively measure mental and emotional health and other life skill competencies. This scoring process is a universal and simple scoring system that helps users evaluate their emotional and mental health and other life skills versus the rest of the population. The purpose of the scoring system is to predict a user's readiness for successfully navigating a life stage. It measures emotional/mental readiness for a particular life stage in much the same way the SAT score is a standard way to measure readiness for college level work.

Up until now, the "intangible nature" of soft life skills made it hard to measure a person's readiness for a life stage, such as going to college, in a universal, meaningful way. For example, upon taking the SAT test, prospective students parents, and the university admissions office review the SAT score to ascertain the student's academic readiness for the rigors of college level work. In the past, there was no easy, universal method to measure such soft emotional and mental skills, such as the ability to set goals and make concrete steps towards those goals or the ability to manage one's schedule or be able to live independently from parents with other college students. First of all, these skills are not easy to measure. Secondly, various efforts to measure this or that soft skill have not become universally accepted as the SAT test is. Further, the limited number of tests that do measure a life step readiness such as marriage compatibility tests are expensive and haven't been standardized. Lastly, these readiness tests are focused on a particular life step. This system of measurement is designed to apply a universal measurement system to any life step.

Examples of the variety of life stages include moving from high school to college, from college to career, or from military service to a civilian career. It is important to quantify a score in these life steps so that a user can measure their own readiness to successfully navigate that life step and/or avoid the problems current statistics say are so common. The baseline success score for each life stage is found by determining the median of the individual skills of those who have/are successfully navigating that particular life step.

A total life step score may be established for every life step that involves increased mental and emotional intelligence and other soft life skills such as self-management and improved interpersonal relationship skills. It provides a means for users to measure readiness to successfully navigate a life step before they take that life step.

The key aspects of the LES scoring process are:

1. Life stage or life step=A stage of one's life that is a transitional event and considered positive according to cultural and societal norms requiring an increase in emotional/mental health and life skills. Examples are: high school to college; college to career; single to marriage; childless to parent; entry level career to management; and military service to civilian career.

2. Disorder/syndrome=Any known psychiatric disorder, diagnosis, or syndrome that impact life efficacy or emotional well-being. Examples are anxiety disorder, PTSD, bi-polar, ADHD, depression, anorexia, etc.

3. Interpersonal skills=Relationship skills that indicate a presence or absence of being able to fill each partner's key primary needs well enough over some time period. Examples are: mutual respect; feel secure; can resolve conflicts satisfactorily; enjoy the time you together; support one another, interest in one another's lives, etc.

4. Self-schema=Beliefs and ideas people have about themselves. Examples are: Self-confidence, self-esteem, self-concept, self-respect, etc.

5. Attitude toward risk=A person's tolerance for possibility of loss or injury. Examples are: risk adverse, risk neutral, risk tolerant, thrill seeking, etc.

6. Self-management=A person's ability to set goals and take steps to achieve them. Examples are: ability to set goals, ability to accommodate failure, etc.

An example table of the LES scores that may be used for the marriage life stage is as follows:

| Component | Baseline score for success (scale of 1-100) | A user's aggregate score (scale of 1-100) | Effectiveness/deficiency gap |
|---|---|---|---|
| Total Life efficacy score for life stage (LES) | 65 | 51 | −14 |
| Disorder/syndrome | 5 | 15 | −10 |
| Interpersonal (IP) skills (out of 25) | 20 | 10 | −10 |
| Self-Schema (SS) (out of 25) | 15 | 18 | 3 |
| Attitude toward risk (ATR) (out of 25) | 15 | 18 | 3 |
| Self-management (SM) (out of 25) | 20 | 20 | — |

Figure 4:
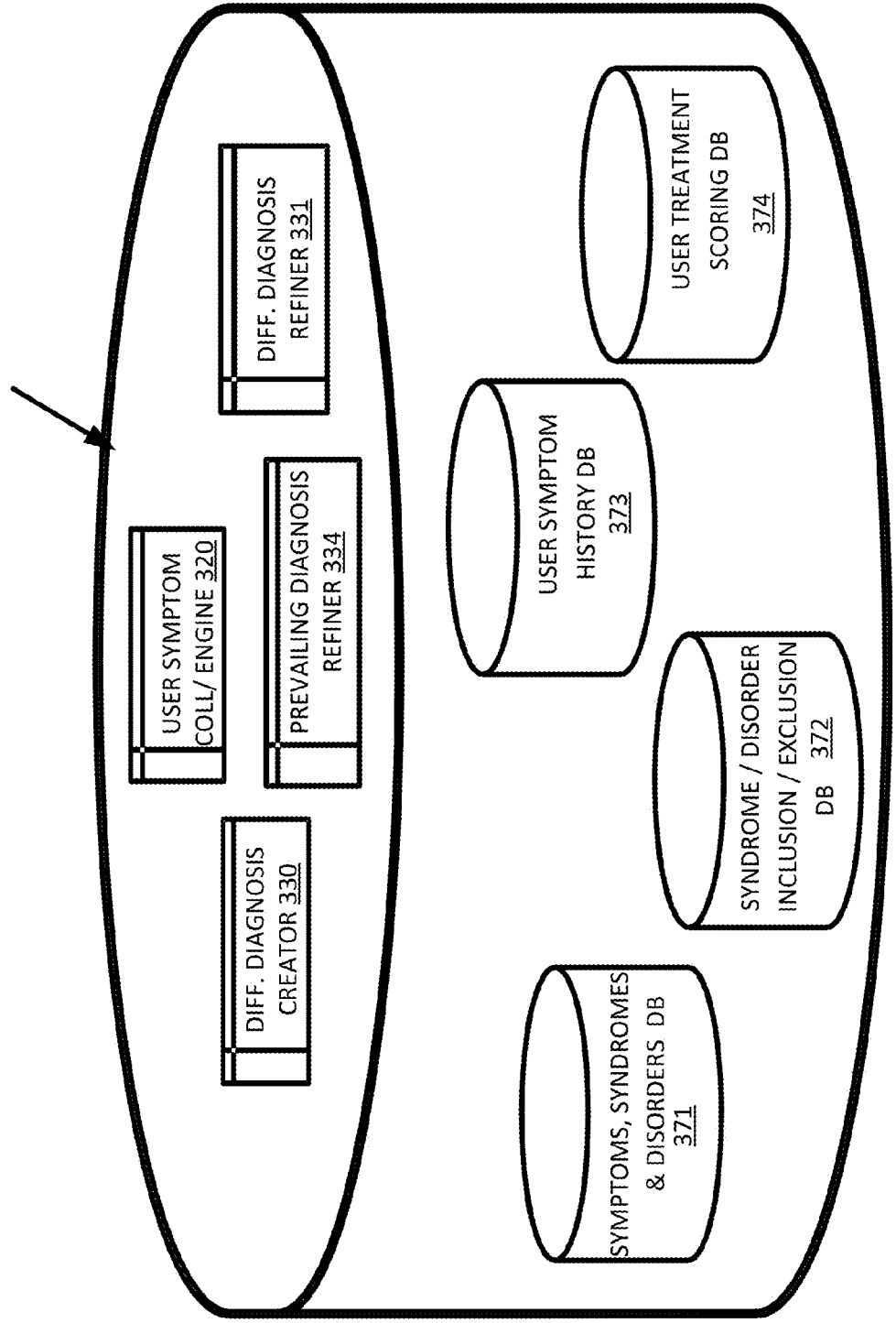
FIG. 4 is a block diagram of one embodiment of the database and application program sub-modules of the reverse engineer diagnosis program module of FIG. 1b.

FIG. 4 illustrates the database and application program sub-modules for the reverse engineer diagnosis program module 300. The symptoms, syndromes, and disorders databases 371 and 372 contain information about known syndromes and disorders and the symptoms and personal characteristics associated with each of them. The user's current symptoms collected by the life stage measurement module 200 may also be stored in a user symptom history database 373. Alternatively, the reverse engineer diagnosis module may collect the user's current symptoms any time he or she accesses the system through another data entry screen and store them in the local user symptom history database. The differential diagnosis creator sub-module then compares the user's current symptoms to the symptoms and other characteristics stored in the syndrome/disorder databases 371 and 372 to create the differential diagnoses. The differential diagnosis refiner sub-module 331 then ranks and prioritizes these differential diagnoses as most likely to least likely. The prevailing diagnosis refiner sub-module 334 then compares all differential diagnoses with the user reported efficacy of treatment following each treatment or training session for each syndrome or disorder identified by the system. Over extended system use, the prevailing diagnosis is the one in which the user scores the treatment as being the most useful or helpful to their personal needs.

The database structure of the Symptoms, Syndromes and Disorders database 371 may include the following fields and the purpose of each field:

| Field Name | Description |
|---|---|
| Disorder = | The name of the label or syndrome |
| Key Symptom1 = | Primary presenting problem |
| Key Symptom2 = | Secondary presenting problem |
| Physical symptoms1 = | Additional physical symptoms |

-continued

| Field Name | Description |
| --- | --- |
| Physical symptoms2 = | Additional physical symptoms |
| Emotional symptom1 = | Current emotional state rating of user |
| Emotional symptom2 = | Emotional state under stress |

Some example content in the Symptoms, Syndromes and Disorders database 371 includes:

| Record no. | Disorder | Key Symptom 1 | Key Symptom 2 | Physical Symptom 1 | Physical Symptom 2 | Emotional Symptom 1 | Emotional symptom 2 |
| --- | --- | --- | --- | --- | --- | --- | --- |
| 1 | PTSD | Flashbacks | Bad dreams | Sleep interruption | Angry outbursts | Guilt | Depression |
| 2 | ADHD | Inattention | Hyperactivity | Sleep interruption | | Low self esteem | |
| 3 | Anorexia | Refusal to keep healthy body weight | Fear of gaining weight | Binging/purging | Overuse diet pills, laxatives | Low self esteem | |
| 4 | Substance abuse | Overindulgence of substances | Lack of focus | Weight loss | | Depression | |

The database structure of the Symptoms, Syndromes and Disorders Inclusion/exclusion database 372 may include the following fields and the purpose of each field:

| Field Name | Description |
| --- | --- |
| Primary demographic characteristic 1 = | Primary demographic trait |
| Primary demographic characteristic 2 = | Secondary demographic trait |
| Heredity factor = | Is syndrome/disorder inherited? |
| Sex factor = | Sex that most frequently experiences this disorder/syndrome |
| Exclusionary symptom = | Any symptoms that exclude a differential diagnosis |
| Inclusionary symptom = | Any symptoms that include a differential diagnosis |

Some example content in the Symptoms, Syndromes Inclusion and Exclusion database 372 includes:

| Disorder | Primary demographic characteristic 1 | Primary demographic characteristic 2 | Heredity influence (Y/N) | Sex Factor | Exclusionary symptom | Inclusionary symptom |
| --- | --- | --- | --- | --- | --- | --- |
| PTSD | Male | Adult | N | N/A | lack of traumatic event | Traumatic event |
| ADHD | Children | Teens | Y | N/A | chronic illness, substance abuse | symptoms always present |
| Anorexia | N/A | Fear of gaining weight | N | F | acceptable BMI | N/A |
| Substance abuse | N/A | N/A | Y | N/A | N/A | Overindulgence of substances |

Figure 5:
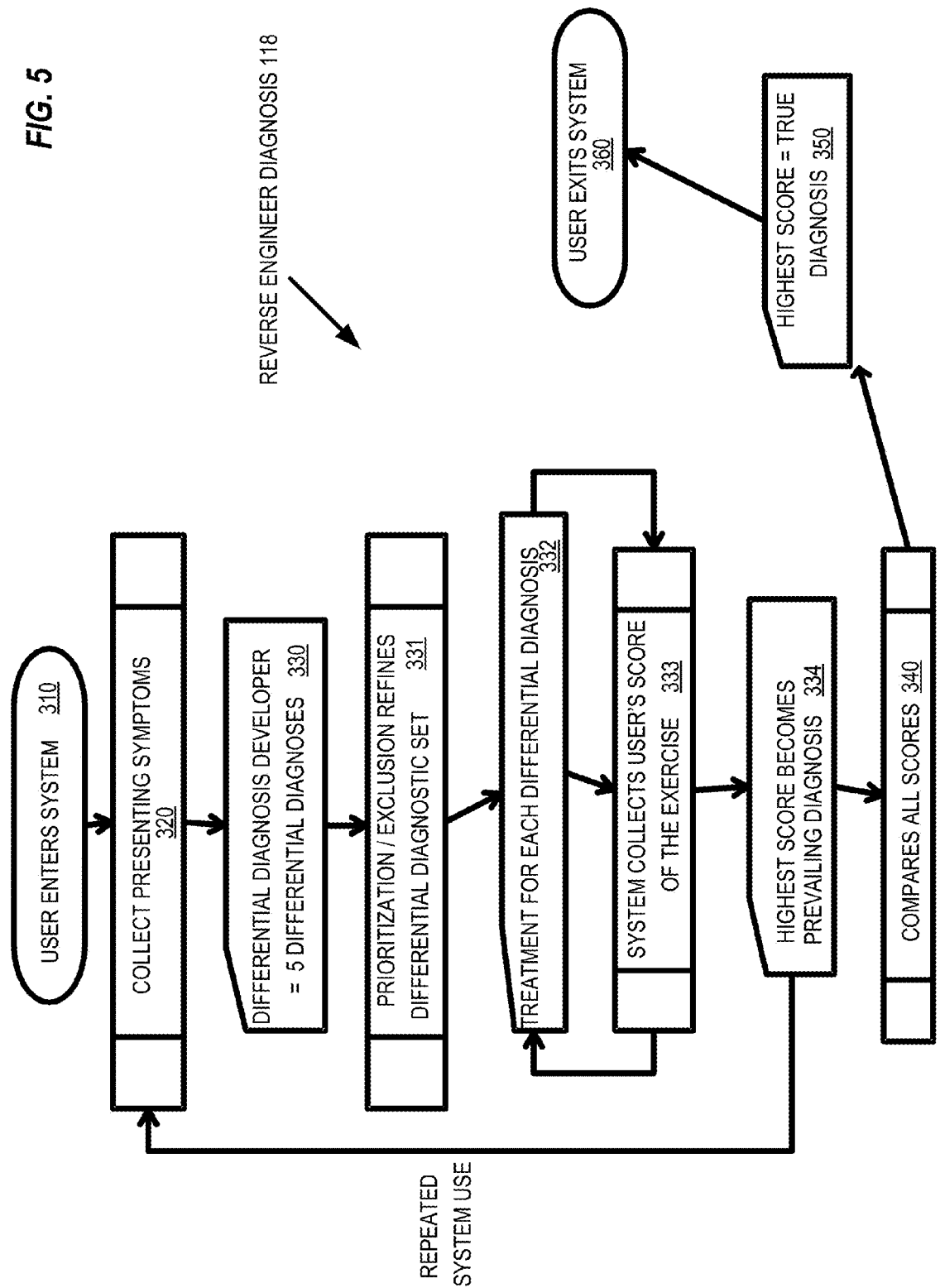
FIG. 5 is flowchart of the method implemented by the reverse engineer diagnosis program module of FIG. 4 to create a "true" diagnosis for each user by reverse engineering a standard diagnostic process.

FIG. 5 is a more detailed flow diagram of an exemplary embodiment of the reverse engineer diagnosis process 118 of FIG. 2 implemented by module 300 described in FIG. 2. In step 310, the user logs into the system 100. In step 320, the module 300 collects a variety of physical and emotional symptoms and other evidence of emotional and mental problems and personality from the life skill measurement module 200 or, alternatively, directly from the user, In step 330, the module 300 compares the entered symptoms to the known symptoms stored in the databases 371 and 372 for each disorder or syndrome and outputs a predetermined set of the closest matching syndromes and disorders, five for example. In step 331, module 300 compares the user's symptoms to the exclusionary/inclusionary symptoms for each syndrome or disorder stored in database 372 and removes those syndromes or disorders that are missing inclusive symptoms or have exclusive symptoms. The system then gives points to each differential diagnosis for having the most of its symptoms and the most intense of its included symptoms. This scoring system ranks the syndromes or disorders in order of most likely to least likely.

In step 332, the user engages with the treatment or training modules to receive treatment therapies or training for each syndrome or disorder, as previously described in connection with FIG. 2. Following each therapeutic treatment or training session, the user is given the chance to rate the treatment or training as far as its value to the user, which is collected by the module in step 333. In step 334, the module determines which treatments received the highest rating by the user for the particular set of symptoms analyzed and the symptom relating to such highest rated treatments is identified as the prevailing diagnosis. The user then repeats the process for each of the ranked diagnoses to generate a score for each of the prevailing diagnoses, which are compared in step 340. The module then outputs the prevailing diagnosis with the highest score as the "true" diagnosis in step 350. The user then exits the system in step 360.

Figure 6:
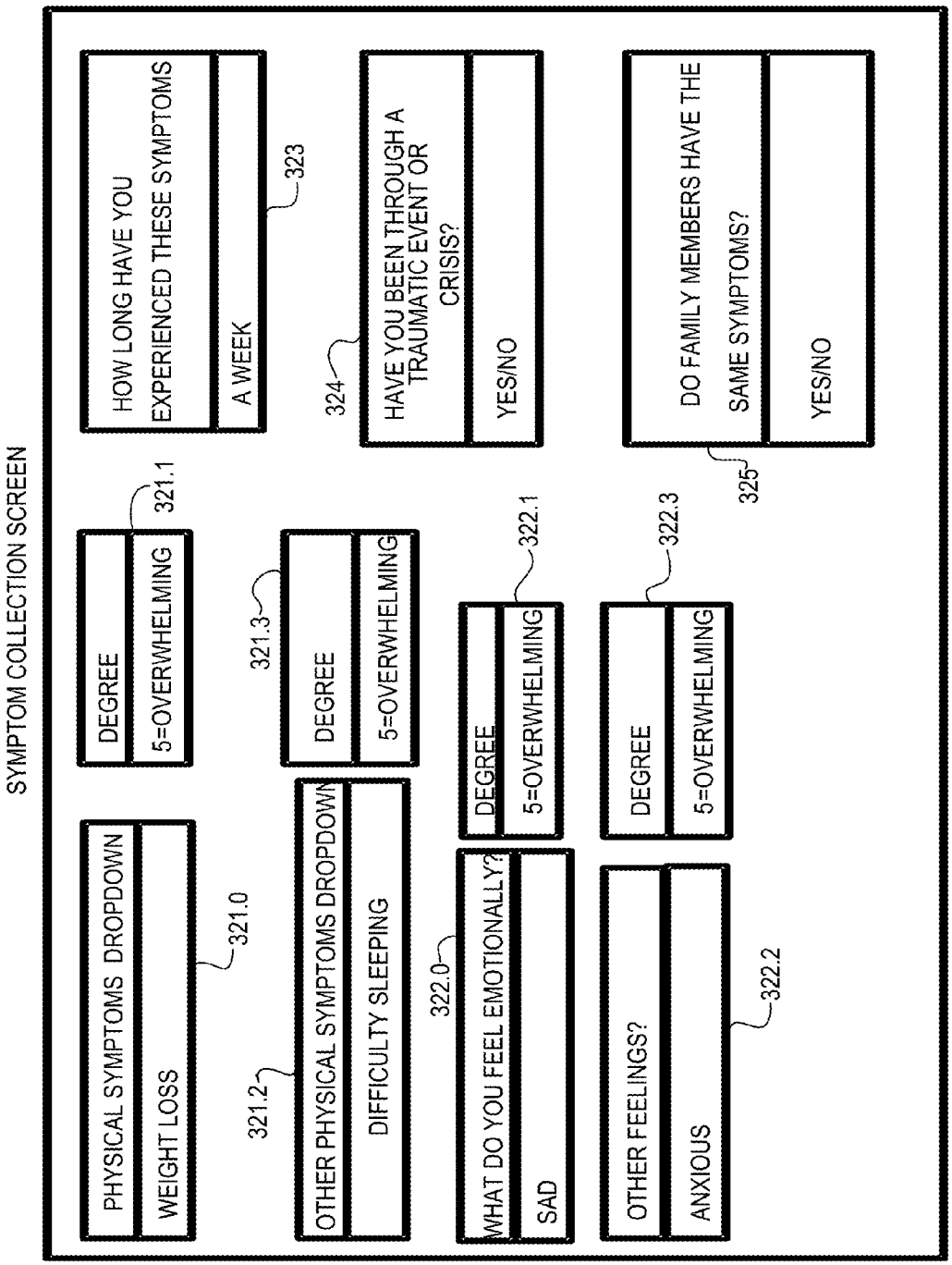
FIG. 6 is an example of an exemplary data entry screen the system may use to collect symptoms and other evidence of emotional and mental problems and personality from the user.

FIG. 6 depicts an exemplary data entry screen either of the life skill measurement module 200 or of the user symptom collection engine 320 of the reverse engineer diagnosis module 300. The system uses the entry screen to collects a user's physical symptoms 321.0, 321.2, etc., emotional symptoms 322.0, 322.2, etc. and the intensity of each symptom 321.1, 321.3, 322.1, 322.3, etc. The data entry screen permits the user to enter a variety of physical and emotional symptoms and to answer a few more diagnostic questions to collect additional pieces of information which can be used in the inclusionary/exclusionary process steps 323, 324, 325 depicted in FIG. 5.

Some examples of these symptoms are:

Physical symptoms: Pounding heart, dizzy feeling, breathing problems, muscle tension over entire body, headaches, loss of interest in sex, persistent aches or pains, digestive problems, no physical symptoms Emotional symptoms include: A persistent sad, anxious, or empty mood; feelings of guilt, worthlessness, and/or helplessness; feelings of hopelessness and/or pessimism; persistent feeling of dread, catastrophe or nervousness; increase in absentmindedness; intense and sudden feelings of panic; can't describe my feelings.

Figure 7:
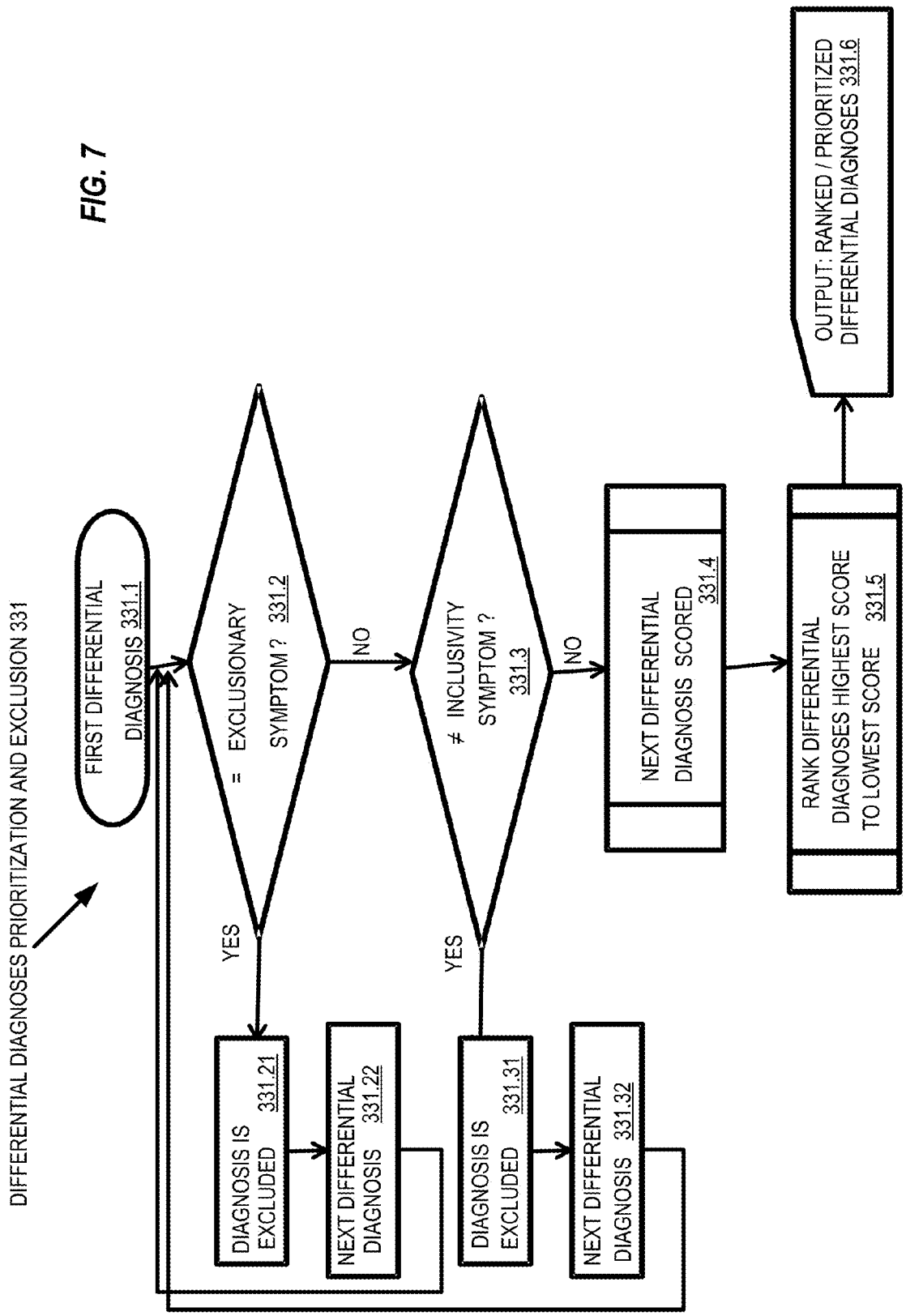
FIG. 7 is a flowchart that details the detailed steps of the differential diagnoses prioritization and exclusion step that refine a group of differential diagnoses into a subset of prioritized and more likely diagnoses.

Intensity degree scale: 1=rarely impactful, 2=sometimes impactful, 3=impactful, 4=very impactful, 5=overwhelming FIG. 7 depicts a more detailed flow diagram which illustrates an embodiment of the process of implementing step 331 of FIG. 5 of scoring each differential diagnosis in order to rank and prioritize the set of differential diagnoses. In step 331.2, reverse engineering diagnosis module 300 starts assessing the first diagnosis of the multiple diagnoses generated. In step 331.2, the module 300 considers whether that differential diagnosis includes certain exclusionary symptoms. If yes, the first diagnosis is excluded from further consideration and the module increments to a consideration of the second of the set of diagnoses generated. If no, in step 331.3 the module 300 next considers whether the first diagnosis does not include inclusionary symptom. If the differential diagnosis does not include an inclusionary symptom in step 331.21, it removes the differential diagnosis from further consideration in step 331.31 and then moves to the next differential diagnosis. In step 331.4 of this process, each differential diagnosis 331.4 is scored in the following manner:

=1 point for each matching physical and emotional symptom to differential diagnosis =1 point for each high intensity symptom that matches primary presenting symptoms for diagnosis =2 points for systems that continue to occur over time.

Lastly, in step 331.5 the module 300 ranks the differential diagnoses 331.5 by the total points scored by each evaluated diagnoses. The ranked diagnoses are then outputted to the user in step 331.6. Examples of the exclusion criteria applied in ranking the differential diagnoses are as follows:

Physical symptom 1: can't sleep
Physical symptom 2: loss of appetite
Emotional symptom 1: life feels hopeless
Emotional symptom 2: want to avoid people
Heredity: no
Recent traumatic event: yes By considering all the symptoms with the syndromes, symptoms, and disorders in the syndrome and disorder database 371, the system develops the following differential diagnoses:

Generalized depression
Substance abuse depression
Bi-polar disorder
Generalized anxiety disorder
PTSD In prioritizing the set of differential diagnoses, the system then compares the user's presenting symptoms with the symptoms of each of the set of differential diagnoses in the inclusion and exclusion database 372. The resulting output is the differential diagnoses ranked in the following order:

1. PTSD
2. Generalized depression
3. Substance abuse depression
4. Generalized anxiety disorder
5. Bi-polar disorder For example, the PTSD diagnosis moved to the top of the list of differential diagnoses because the user responded that he or she had recently been through a traumatic event which is an inclusionary key symptom for PTSD.

Figure 8:
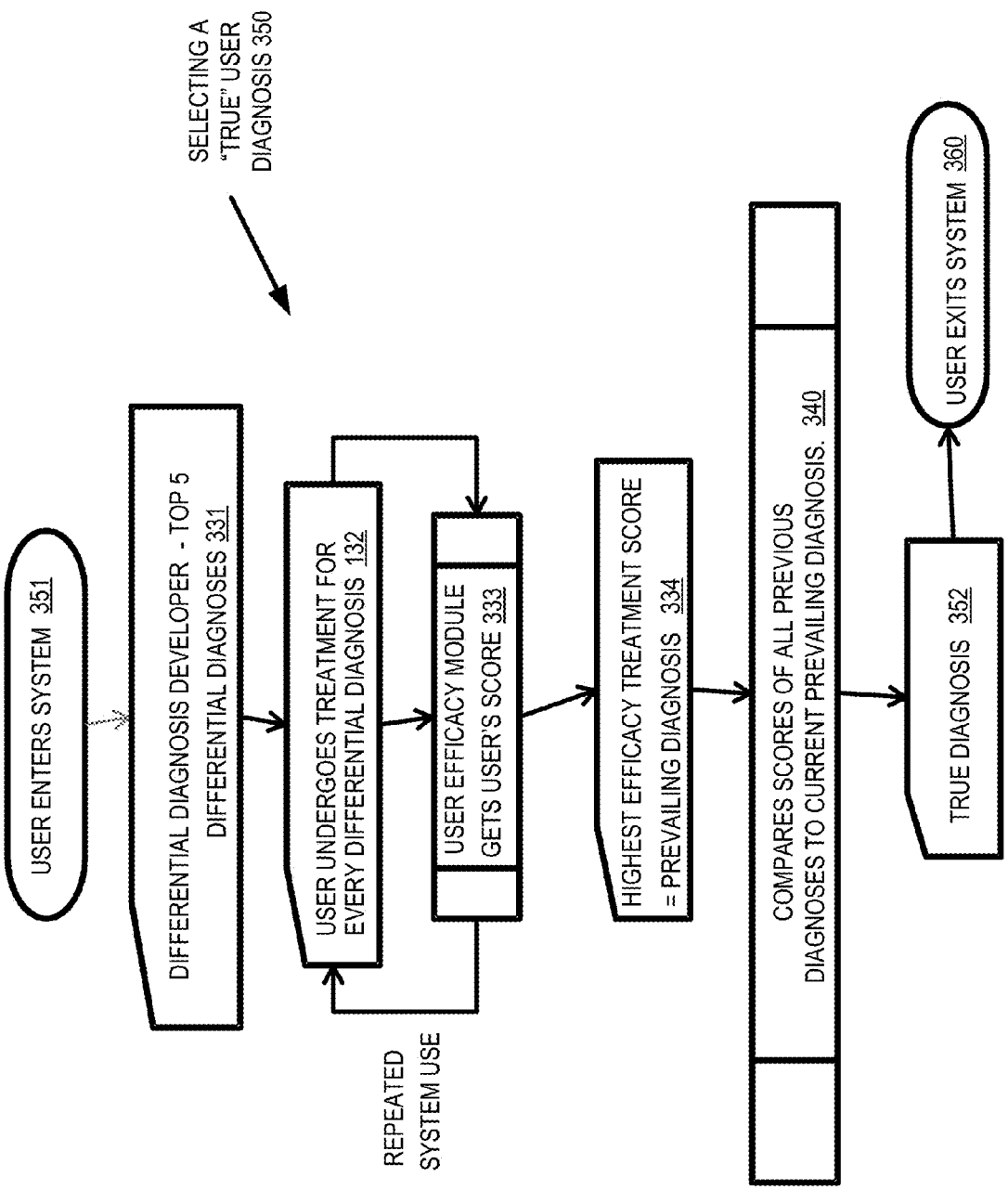
FIG. 8 is a flowchart that illustrates the scoring process of the reverse engineer diagnosis module of FIG. 4 which generates the "true" diagnosis.

FIG. 8 depicts a flow diagram illustrating the method of selecting from a ranked set of differential diagnoses a "true" user diagnosis. A user enters the system 351 and provides the system with their current presenting emotional and physical symptoms and other evidence of the user's emotional and mental health as previously described. In step 331, the reverse engineer diagnosis module 300 develops a series of differential diagnoses based on the user's presenting symptoms and outputs a ranked set of differential diagnosis. In step 332, the module 400 first provides a treatment session for the highest scoring differential diagnosis. After the user has completed the therapeutic treatment session, in step 333 the user treatment efficacy refiner module 700 elicits from the user the user score for the treatment session the user just completed. The system then provides a therapeutic treatment session for the next differential diagnosis. Again the user treatment efficacy refiner module 700 in step 333 elicits the user score of that session. This process continues until the user has scored the treatment sessions for each differential diagnosis. The prevailing diagnosis refiner sub-module 334 then considers the scores of all of the therapeutic exercises the user completed. In step 352, the diagnosis associated with the therapeutic treatment session with the highest user score over multiples uses of the system is generated, which is indicative of the "true" diagnosis for this user and their current presenting symptoms 352.

Figure 9:
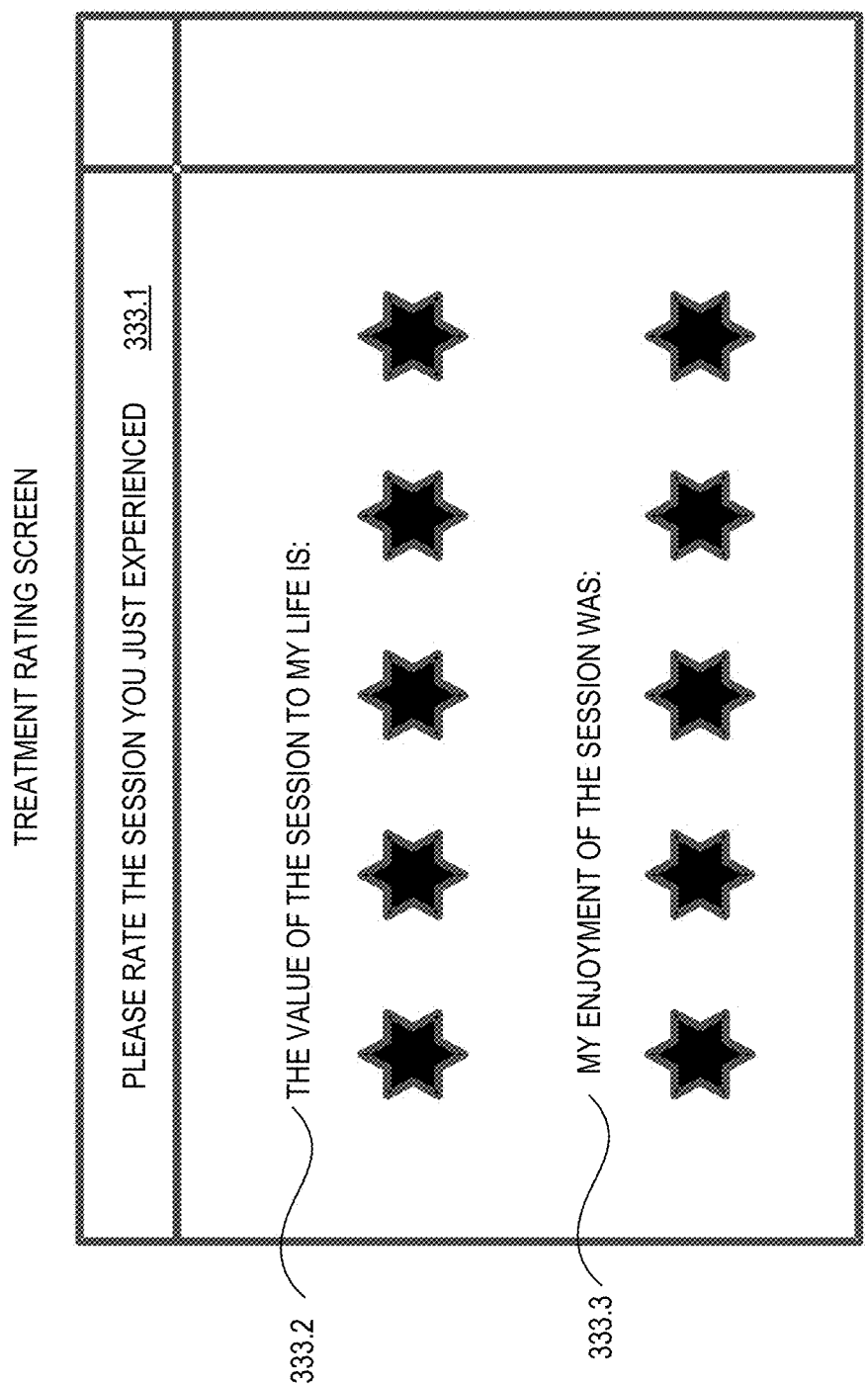
FIG. 9 is an example of the data entry screen the system may use to allow the user to score the various treatments the user may complete using the system of FIG. 1b.

FIG. 9 is an example of the data entry screen 333.1 used in step 333 to gather the data of each treatment the user completes 333. This entry screen 333.1 allows the user to rate of the efficacy of the therapeutic treatment session in fields 333.2 and his or her enjoyment of the therapeutic treatment session just completed in fields 333.3.

Figure 10:
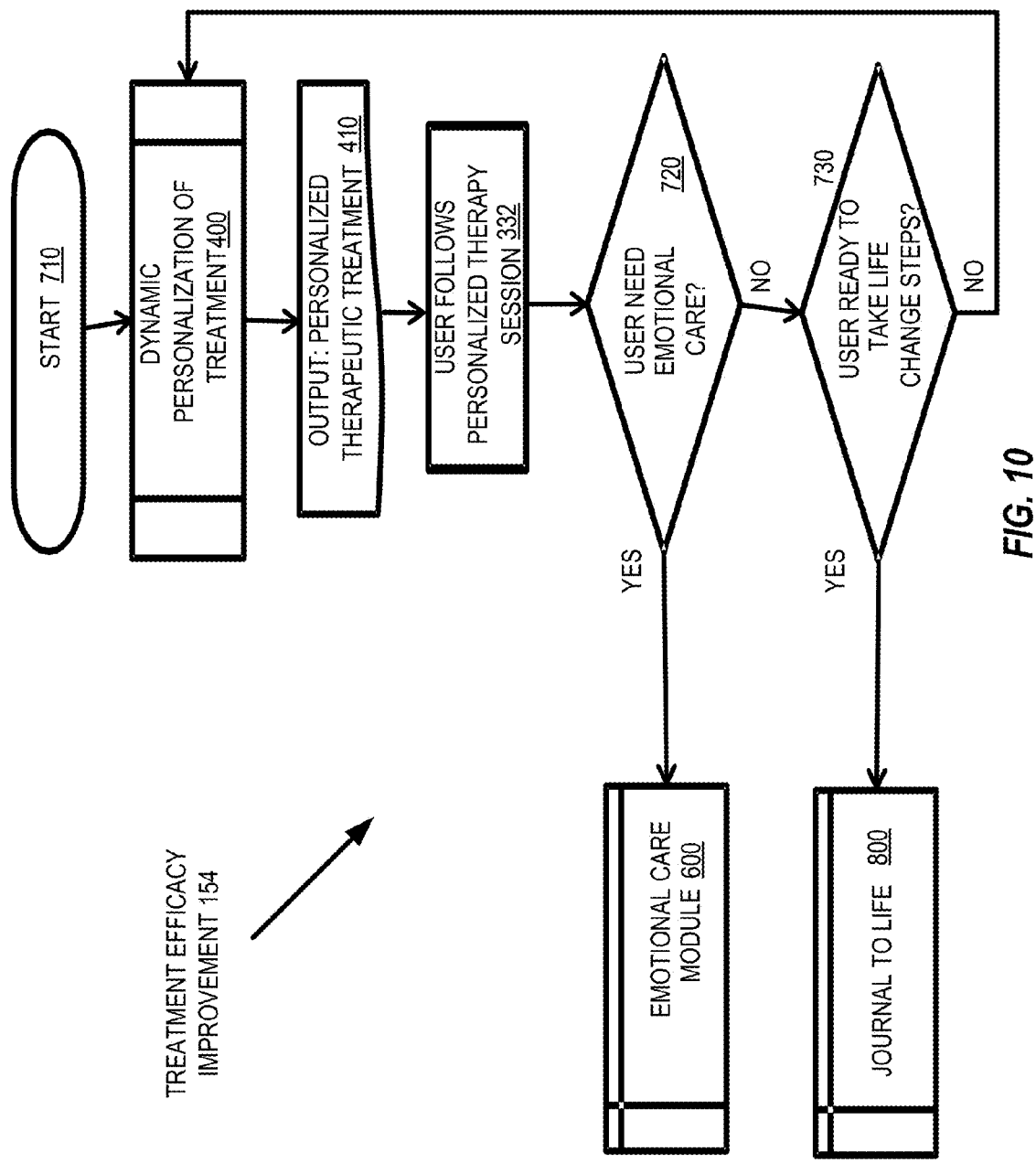
FIG. 10 is a flowchart of the process implemented by the efficacy treatment refiner module of FIG. 1b used to improve the efficacy of online therapeutic treatment programs.

The efficacy scale (the value of the treatment session to the user's needs and life) may be:

1 star=Useless
2 stars=Not very helpful
3 stars=Did some good
4 stars=Useful, helpful
5 stars=Very helpful The enjoyment scale of the session may be:

1=Hated it
2=Did not enjoy
3=Neither like or dislike
4=It was good
5=Very enjoyable experience FIG. 10 is a flow diagram that illustrates the process 154 implemented by the treatment efficacy refiner module 700 to improve the efficacy of therapeutic treatment sessions recommended to the user. In step 710, the user enters the system. In step 332, module 400 selects the best therapeutic treatment program for a user's personality and preferences. The output 410 is a therapeutic treatment that matches each user's personality traits. Following a treatment session, in step 332 the user rates the treatment and in step 720 ascertains if the user needs care for a negative emotional state, which occasionally may have been caused by the therapeutic treatment. If yes, the user is directed to the emotion care module 600 to determine the type of emotion care needed and then provides the user with a treatment process for reducing the type of negative emotions identified, thereby helping the user cope with their negative emotion. This feature will improve the user's desire for additional mental health care from the online system 100. If no, the users is guided to the Journal to Life module 800 module in step 730 which will teach user new life skills as it treat a user's syndromes and disorders. By helping the user learn how to recover from negative emotions, the user will enjoy mental health and emotional growth. This will prompt the user to continue using the system and therefore become a stronger emotional and mentally capable person.

Figure 11:
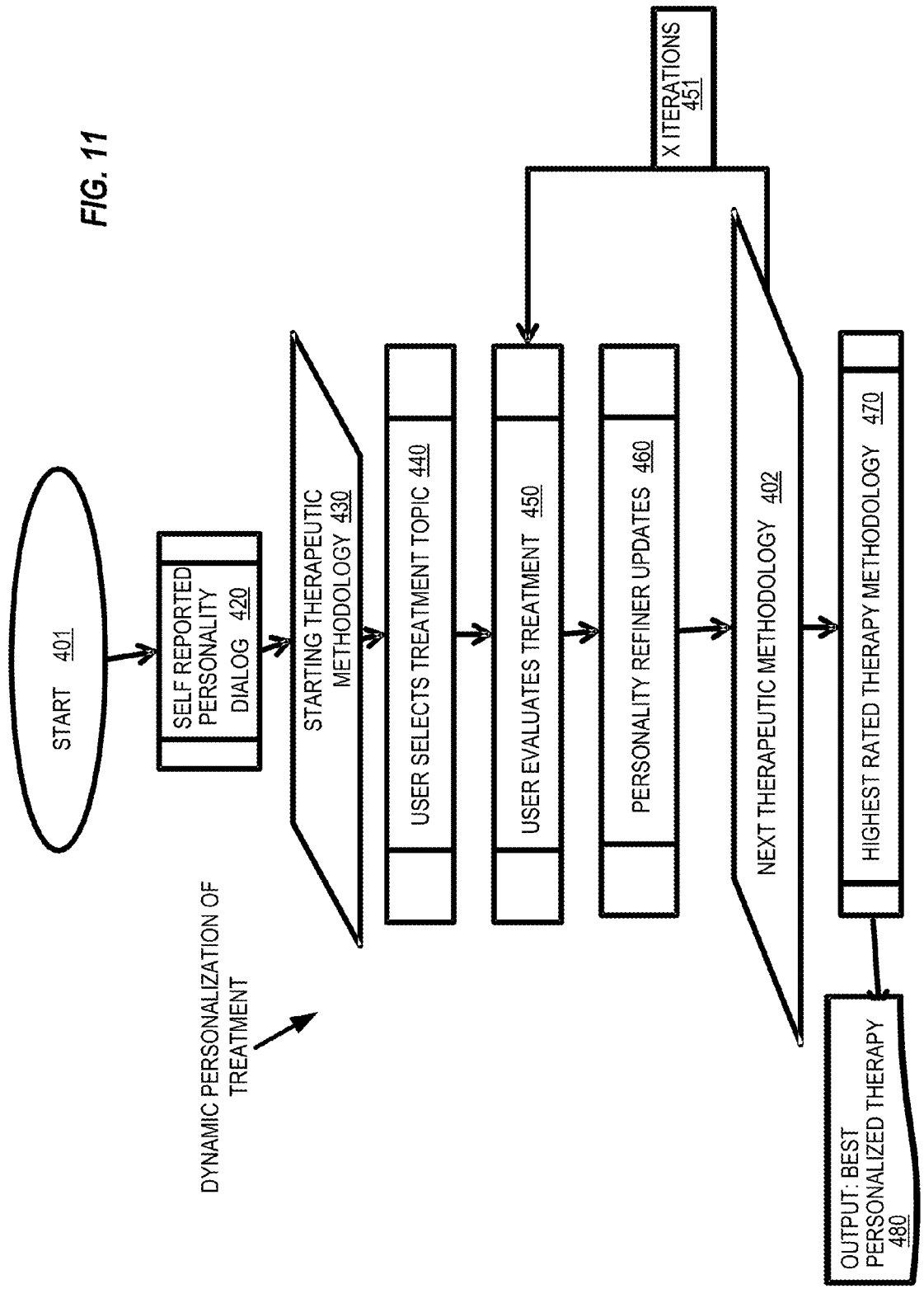
FIG. 11 is a flowchart detailing one aspect of the process of the treatment efficacy improvement module, which dynamically personalizes each treatment to an individual's personality and preferences.

FIG. 11 is a flow diagram that illustrates the process implemented by the dynamic treatment module 400 that matches the therapeutic treatment to a user's personality and preferences. In step 401, the user enters the system and through the use of a self-reported personality dialog data entry screen, in step 420 elicits the user's understanding of their personality traits. In step 430, these traits are matched to some known therapeutic treatment methodologies such as cognitive behavior, operant conditional therapy, psychoanalysis, and positive psychology to name a few treatment methodologies.

In step 440, his user interactively engages in a therapeutic treatment session which is based on their symptomology and the current therapeutic methodology that matches the user's personality. In step 450, then the user is then given the opportunity to rate that therapeutic treatment. In step 460, the module presents to the user a dialog screen that describes a real life scenario. Depending on the user's answers, the personality traits will be confirmed or altered. For example, a user may think they are extroverted. However if the user is given a scenario in which they are among many strangers and the user dislikes that scenario, the indications are that the user's personality may be closer to introverted than extroverted. The system or user in step 402 may then select a different therapeutic treatment program which utilizes a different treatment methodology.

After the user has gone through many personality refining questions and many iterations 451 of the therapeutic exercises, the system will collect enough data to determine which therapeutic methodology the user prefers or is best for their mental health treatments. In step 470, the system will consider the user's scores on all of their therapeutic treatments to determine the best personalized therapy and, in step 480 will begin to offer the therapeutic methodology that has continually scored the highest ratings from the user's regular use of the system.

Figure 12:
FIG. 12 is a data entry screen that may be used to solicit a user's personality traits so the system may customize the therapeutic treatment to that user's personality.

FIG. 12 is an illustrative example of a self-reported personality traits data entry screen 465. The system delivers personality revealing questions to the screen in fields 461, such as for example, if the user considers their personality to be more introverted or extroverted. In fields 462, the system asks questions regarding another personality trait, such as personal motivation. Some people are motivated to please people. Other people are motivated to accomplish goals, objectives or to get rewards. The dialogue through the screen elicits a user's understanding of some of their personality traits. Additionally the dialog seeks to gauge the user's perceived level of these traits in fields 463 and 464 by offering a means to numerically measure the intensity of the personality traits.

A database with the following fields tracks both the self-reported personality traits and further refinements to those answers with additional system use. The two key fields are:

| num_interrelate |
|---|
| num_motivate |

If the user selects fields "introverted" 461.1 or "tangible rewards" 462.2 as their personality type characteristics, the system negates the value in the "degree" answer box and records the degree value in the aligned personality database field. Otherwise, if the user selects that they are "extroverted" in field 461.2 or "motivated by praise from people" in field 462.1, the system records the actual value the user selects as the degree of each personality characteristic in the aligned fields. The results of the database contents are:

| | |
|---|---|
| If num_interrelate > 0 | the user is extroverted |
| If num_interrelate <= 0 | the user is introverted |
| If num_motivate >0 | the user has answered a people pleaser |
| If num_motivate <=0 | the user has answered they are data-driven/goal oriented |

Figure 13:
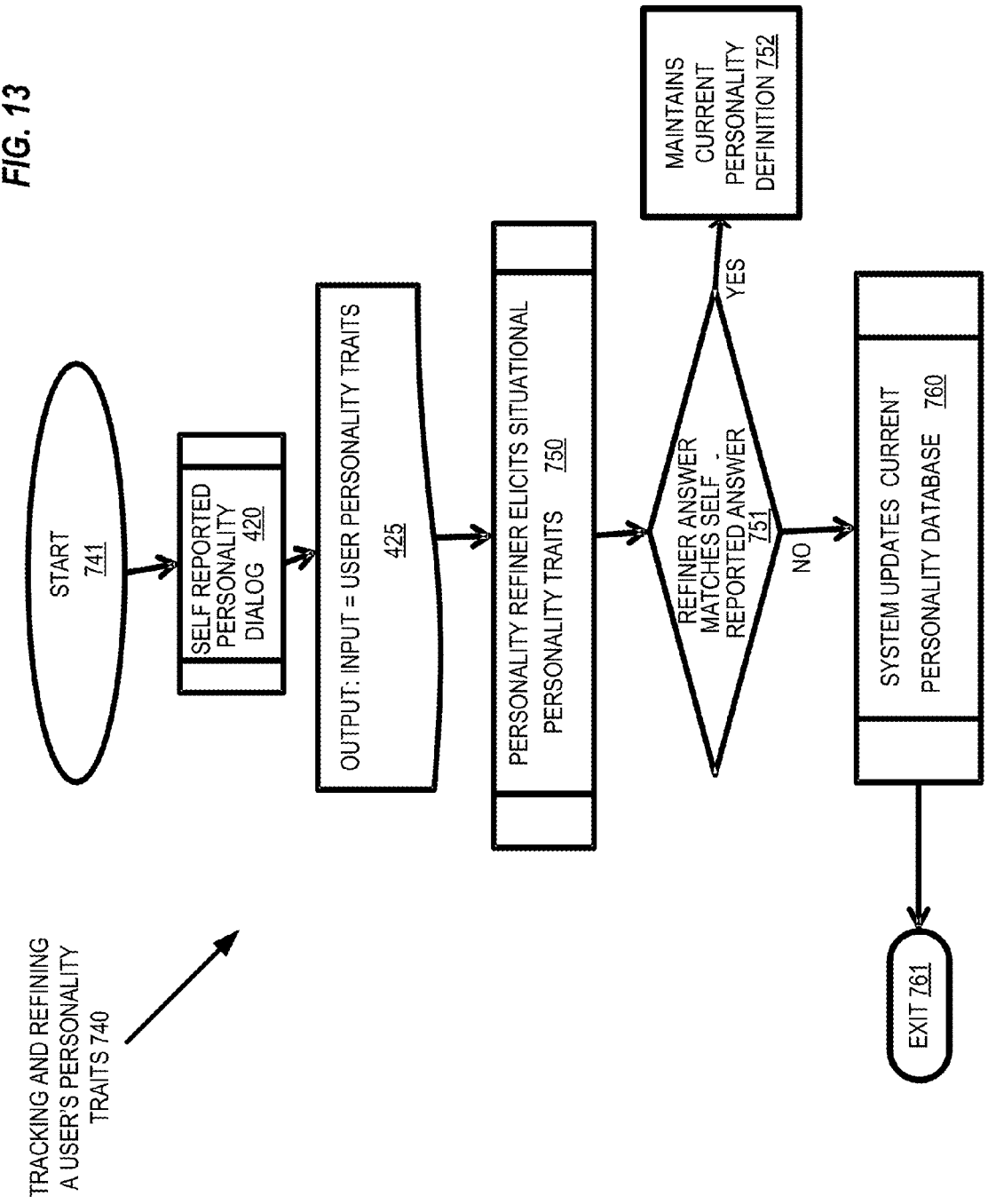
FIG. 13 is a flowchart detailing how fields in a database tracks a user's initial personality definition and then how the fields may be altered as the user's answers to personality refining questions reveal discrepancies to the user's initial personality answers.

FIG. 13 depicts a flow diagram 740 that illustrates the process of tracking and refining the current personality traits of each user. In step 420, the system receives information about the user's personality as a result of the user populating the personality database fields of the self-reported personality dialog screen with user responses, and in step 425 outputs the user's personality profile or traits. In step 750, the system 100 presents a random series of dialogs to the user. Each dialog describes a real world setting. The user is then asked how they respond to this real world setting. If the user is in tune to his or her personality and is self-aware, the answers to the dialogs confirm the previously entered self-reported personality traits. The system may then refine the answers by adding the value associated with each answer to the matching personality database field and then in step 751 determine if the self-reported personality traits need to be refined. If the answers to the dialog confirm the user's responses to the self-reported personality dialog 752, the system in step 752 maintains the existing personality definition or profile. If the dialog answers do not confirm the self-reported personality, the system will alter the definition of the user's personality based on the scored personality traits described above in step 760. The user then exits the system in step 761.

FIG. 14 is an example of a questionnaire date entry screen 750.1 that may be used for refining the personality traits of the user. By placing the user in a real world setting, the system gauges how insightful the user is concerning their personality traits. Each answer to the question/scenario is given a numeric value as described below. These numbers are added to the existing personality trait numbers to confirm or alter the user's true personality trait. An example of how the database fields for the user's interrelational personality makeup is recorded in a user personality profile score database:

750.11 num_interrelate=existing num_interrelate value+−2

750.12 num_interrelate=existing num_interrelate value+−1

750.13 num_interrelate=existing num_interrelate value+0

750.14 num_interrelate=existing num_interrelate value+1

750.15 num_interrelate=existing num_interrelate value+2

FIG. 15 is a chart 755 describing how the system matches the user's personality definition to a school of therapy. This matching is used as a starting point so that the user's therapy session connects to the user in a way that matches the user's personality. Psychoanalysis and cognitive behavior therapies tend to deal with feelings and introspection while positive psychology and operant conditioning therapies tend to be less introspective and more action or externally oriented.

The therapy school to personality matchup is as follows:

| Personality Traits Are | Starting therapy methodology | |
|---|---|---|
| 755.1 Extroverted + People/acceptance | Cognitive Behavior | 756.1 |
| 755.2 Extroverted + Data/goal | Positive Psychology | 756.2 |
| 755.3 Introverted + People/acceptance | Psychoanalysis | 756.3 |
| 755.4 Introverted = Data/goal | Operant Conditioning | 756.4 |

During the same session, the user is provided the opportunity to choose the same therapy topic (such as lose weight or stop smoking) using other schools of therapy starting with the schools that are close to the user's personality profile. Because the system continues to query the user about their personality and preferences, the system will gain a more complete definition of the user's personality traits. As the system continuously seeks the user's evaluation of each therapeutic session, the system will gain an understanding as to which therapeutic methodology a user finds the most beneficial.

Figure 16:
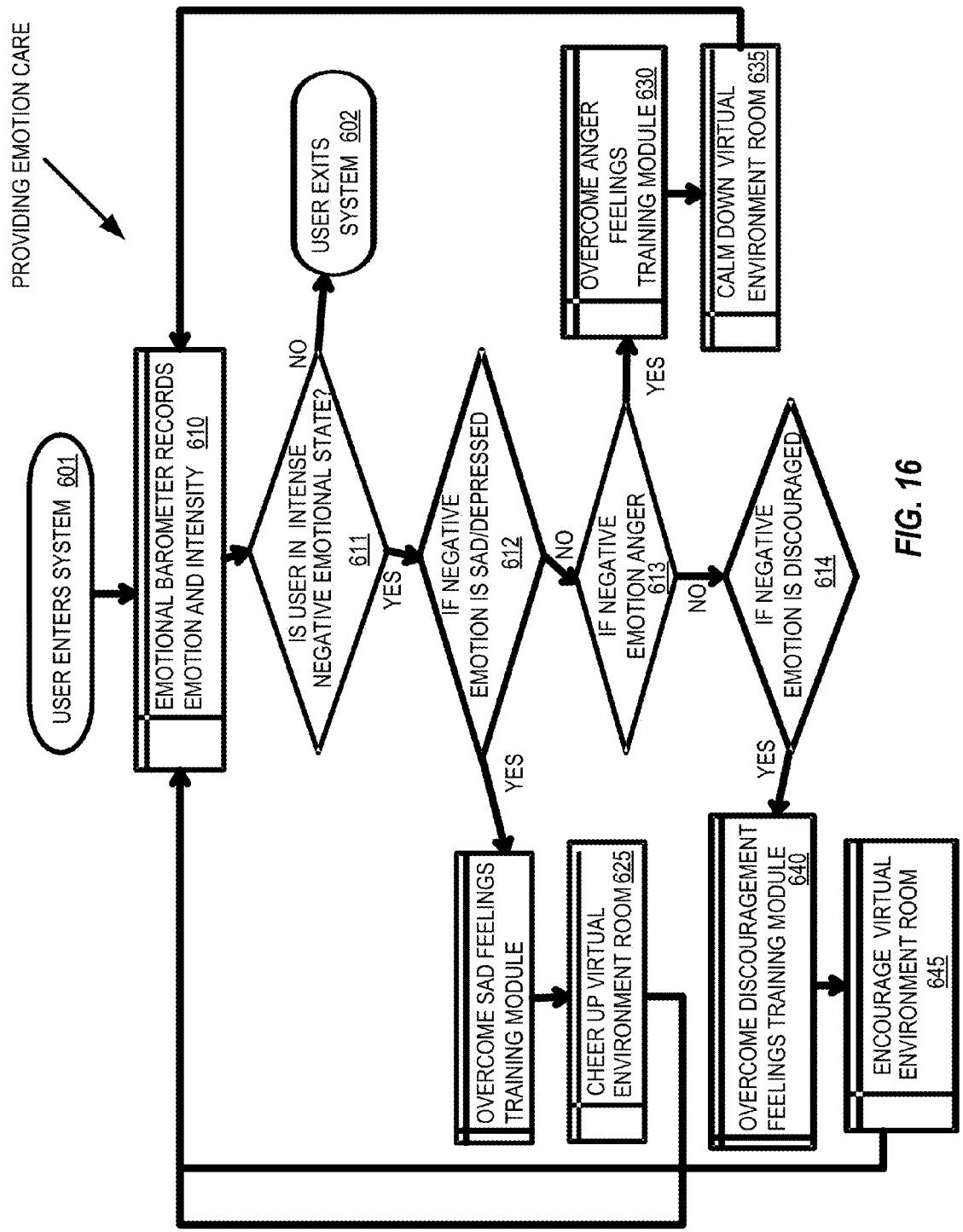
FIG. 16 is a flow diagram of the process by which the emotion care module finds and handles negative emotions that may occur during the time the user is getting treatment from the system.

FIG. 16 is a flow diagram of an illustrative process for providing emotional care through the emotion care module 600. Users that are going through therapy occasionally feel sad, angry, anxious, or depressed as they cope with unpleasant or other negative areas of their past or current lives. If the system detects the user is in a negative emotional state, the system in step 601 guides the user to the emotion care module. In step 610, an emotional barometer program and data entry interface screen of the module provides the user a means to convey their emotional state to the emotion care module 600.

The user responds to the emotional barometer queries with his or her current emotional state and the intensity level of the emotions. In step 611, if the module detects that the user is in a negative emotion state, the system then evaluates the intensity level. In steps 612, through 613 if the module registers a high intensity negative emotion of a specific negative emotion, such as sadness/depression, anger, or discouragement, the module directs the user to a virtual negative emotion improvement room. For example, if the module registers a depressed user, in step 612, the user is directed to an "Overcome sad feelings" virtual training module 620 or a Cheer up virtual environment room 625. In the event the negative emotion is anger, in step 613 the module directs the use to an "Overcome anger feelings training module" 630 or a "Calm down virtual environmental room" 635. In the event the negative emotion is discouragement, the module in step 640 directs the user to an "Overcome discouragement feelings training module" or a "Be encouraged virtual environment room" 645. The system allows the user to stay in each selected negative emotion care room until they are ready to leave. In step 602, the user exits the system.

Figure 17:
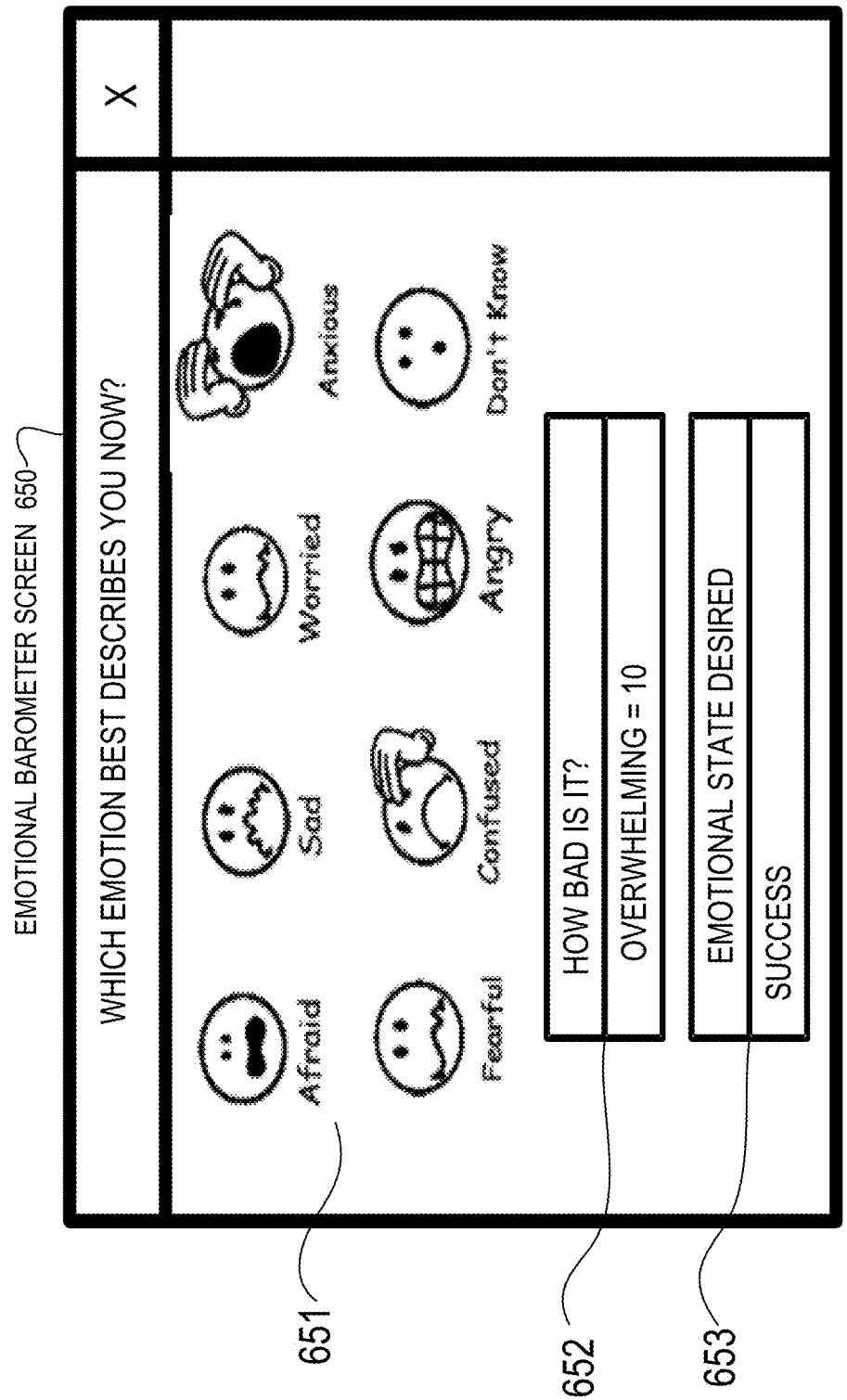
FIG. 17 is an example of a data entry screen the user may see when the system solicits the user's emotional state and intensity for the purposes of eliciting negative emotions and handling the negative emotions in a positive way.

FIG. 17 is an illustrative example of the emotional barometer data entry screen 650 of the emotion care module. This screen provides a simple menu that displays a variety of negative and positive emotion fields 651 along with images of faces that are conveying that emotion. Next in fields 652 the user is asked how intense the negative emotion feels and also in fields 653 which emotional state the user desires. The responses to this menu cause the module to put the user into the appropriate negative emotion virtual training room. The user may stay in this virtual training room for as long as they desire until they feel their negative emotion subside.

Figure 18:
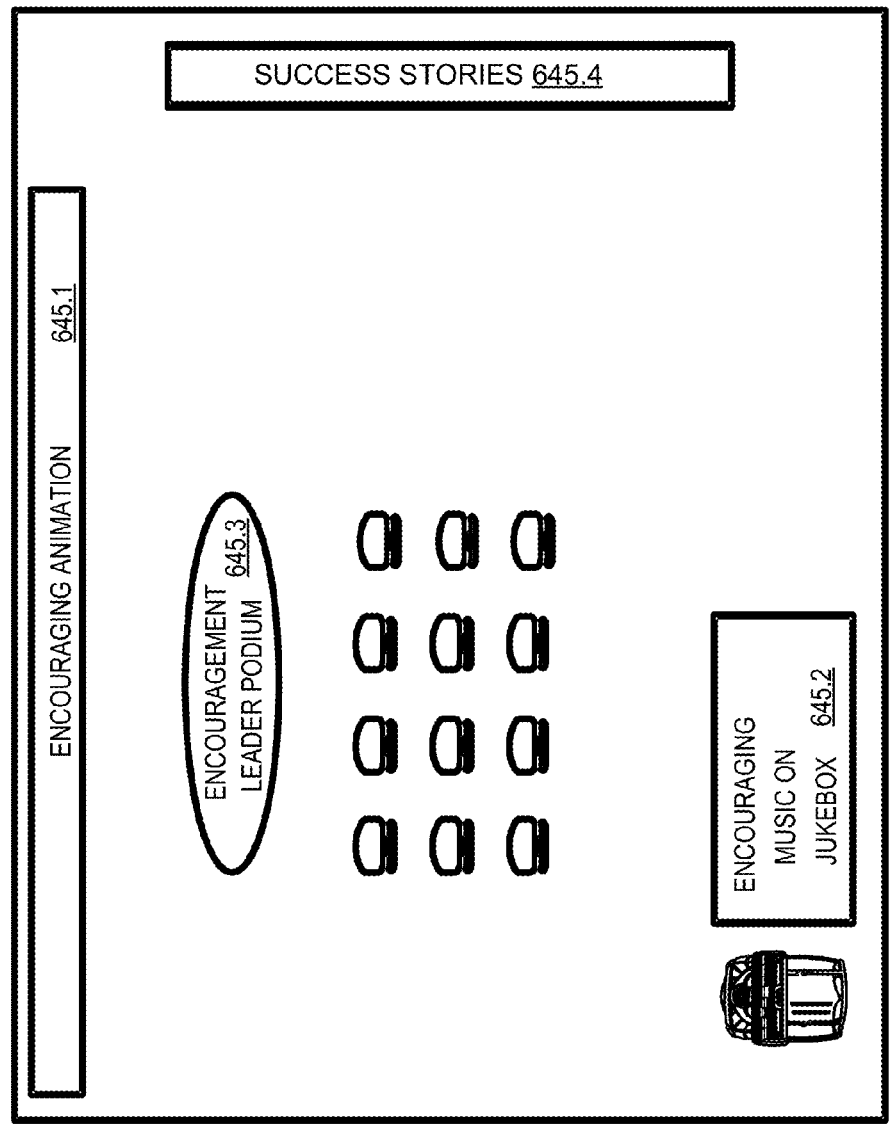
FIG. 18 is a schematic diagram of the features in a web-based room that is used to coach and encourage a user as he or she is dealing with negative emotions.

FIG. 18 is an illustration of one of the negative emotion virtual training rooms. The room illustrated is specifically the Virtual Encouragement Room 645. Room 645 has many tools and features that help the user deal with his or her negative emotion. The virtual room 645 may have a few creative touches such as encouraging and uplifting music 645.2, encouraging posters 645.1, lots of success stories 645.4, and training sessions from a video or a real person 645.3 in which the users are coached in a variety of techniques to overcome their negative emotions and build the wherewithal to go back into their lives, accomplish their dreams, or get beyond their barriers.

Figure 19:
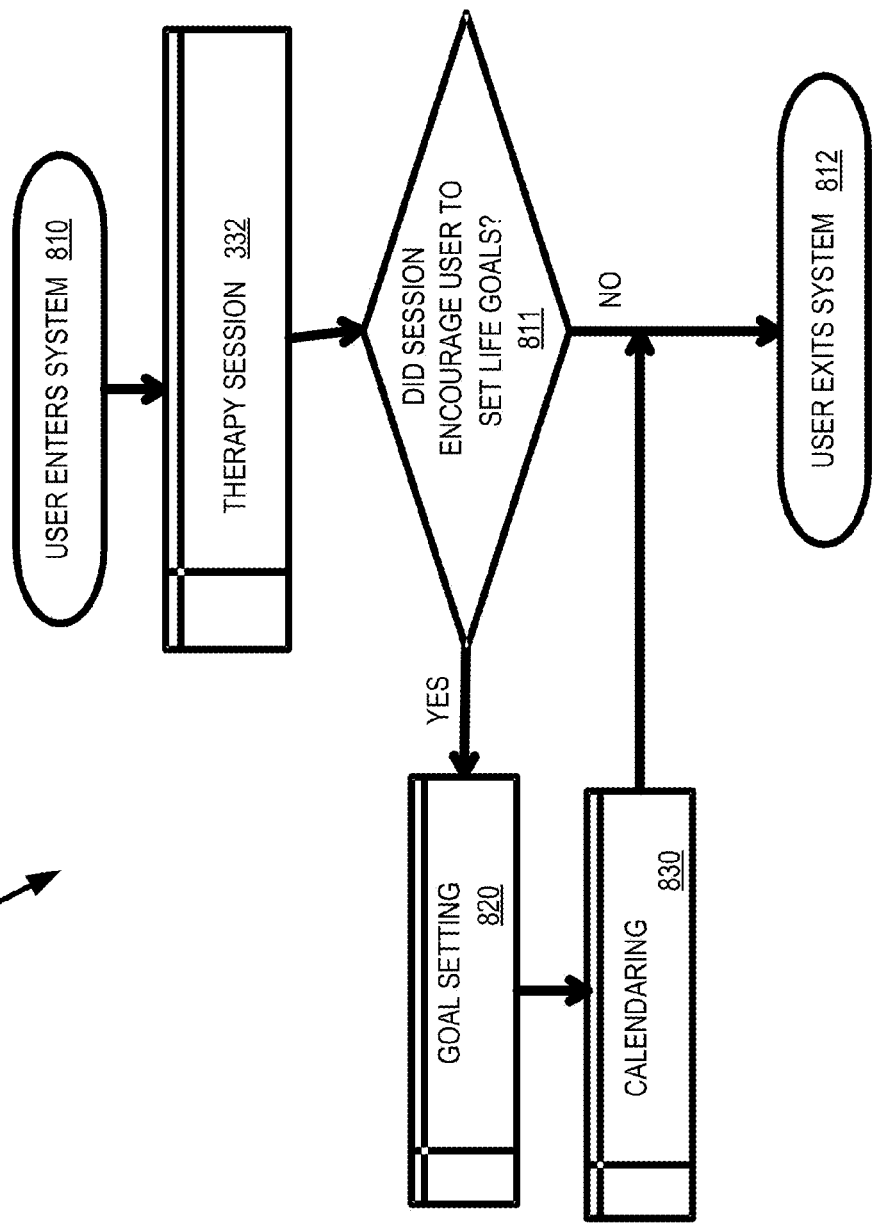
FIG. 19 is a flowchart of the process implemented by the Journal to Life module that teaches the user how to set life goals and take practical steps that change the user's behavior such as scheduling a task or setting up reminders in the user's calendar.

FIG. 19 is a flow diagram illustrating the process 802 implemented through the Journal to Life module 800 of the system to determine goals for their life and identify milestones to implement their goals to their schedules, thereby guiding and training the user to make positive life changing decisions. The last step 332 of the therapy treatment sessions or life skills training sessions include a set of suggestions concerning various ways the user can apply the content to their lives in a meaningful way. At the completion of the therapy session, the user in step 811 is given the opportunity to take this content and take steps toward incorporating it into their lives. If the user answers "yes" to a question such as for example "Did the session encourage user to set life goals", the system in step 820 teaches the user how to set meaningful goals, milestones and tasks. After the user has created appropriate goals, milestones and tasks, the system in step 830 guides the user to calendar dates and reminders in a personal digital assistant or other calendaring device so that the new changes they desire from their therapy sessions intersect with the user's day to day schedule and activities.

FIG. 20 is an illustrative example of a data entry screen for the calendaring process. The data entry screen guides the user through the process of setting goals in fields 820, milestones in fields 821, and individual tasks in fields 822 then guides the user as to how to quantitatively make the sum of the tasks equal the goal being completed. Additionally, the system allows the user a variety of ways, such as reminders in field 824 to remind them of the goals and tasks to further enable the user to take the therapy concepts and apply the therapy in a meaningful way to each person's lives and to identify rewards in field 823 for successfully completing a given goal.

In summary, the system provides a user with the ability to recognize deficits in his or her critical life skills or emotional and mental health, then guides them to therapeutic treatment and training program modules to improve their ability to successfully navigate a life transition or life event. Additionally the system provides the user with quantitative measurements so that a user can see if progress in being made in his or her life skills or emotional and mental health, thereby help helping the user identify mental and emotional deficits before one's life is seriously impacted.

The scoring engine, educational materials and online tools help users understand any gaps they have in soft life skills compared the population of people who are successfully navigating similar life steps. The system and methods teach users techniques to cope with life obstacles as guides teach them steps to take when they are stymied or find their emotions are limiting their ability to reach goals they desire.

Additionally, the system and method assists the user to negate personality challenges a user may have with a human therapist. The system includes a personality neutral and nonjudgmental avatar "guide" that aids the user through the system. The system permits the users freely to move through the system at a pace that is comfortable and convenient to them. The methods includes treatment methods that occur in the virtual world, which add enjoyment and privacy to the user's treatment experience, which hopefully will convince users to devote more time to therapeutic treatments rather than driving to a clinic to meet with a stranger at a set period of time. The system provides the users with the capability to access emotional and mental health care solutions at any time they feel overwhelmed and for as long as they desire.

There are three ways to evaluate therapeutic treatment: (i) research by the scientific community, (ii) an end user's valuation of this or that treatment module as reported via surveys and the frequency of use, and (iii) the increase in emotional health experienced by the user as measured by lessening negative moods and the ability to successfully navigate life challenges that before have overwhelmed the user. The ranking/scoring module of the present invention takes the wealth of available therapeutic treatments, and then provides a means for the end users to report on their satisfaction with the treatment both with a score and by the frequency they engage this or that treatment or therapeutic methodology. Additionally the novel LES scoring system provides a means to measuring progress made in the following areas: self-management and goal setting, reduction in interruptions from disorders/diagnoses, improvement in attitude towards risk/reward and improvements in self-image. As a user engages this or that particular treatment module, they can also note changes in their life efficacy score. As this scoring methodology becomes wide spread, it can be included as part of preparation for college for all incoming students, preparation for marriage, preparation for starting a career or any event that requires increased interpersonal skills and increased emotional intelligence. The baseline scores will organically evolve as thousands of users access the system and report their responses to every module.

The system will also allow for much more research to be conducted than could be carried out with human researchers alone, thereby improving mental health care. Current research indicates that the skills of the therapist are more predictive of a positive mental outcome than are the specific therapeutic treatments applied to a patient. Given that diagnosis and therapy are almost always attached to a human therapist, there exists little quantitative means to evaluate purely one therapeutic methodology versus another therapeutic methodology. For example, a question that remains unanswered is: is a Positive Psychology treatment regimen better for treating an anxiety disorder than is a Cognitive Behavior treatment regimen? What disorders respond the best to psychoanalytical therapy? Having a system that can be used by millions of people without therapist intervention and who are surveyed at the end of their treatment and whose negative emotional state is measured on a regular basis will generate databases that can be used to provide greater insight into the value of various therapeutic methodologies.

Long term, this system will provide the most value when used in conjunction with a human therapist. This system does not provide a diagnosis. It leads users to a variety of therapies based on their presenting symptoms. As this system is adopted by the therapeutic community, the system will permit one therapist to having an increased number of patients while also increasing the quality of care. Currently the number of patients seen by a therapist is limited because the therapist attendance is required at every therapeutic session. A typical therapeutic session is one hour for a specific number of times a week. Many times the number of sessions is limited (dictated) by an insurance company. With the present system, the therapist can treat more patients at one time as they integrate the use of the system into their therapy sessions and "prescribe" which therapy methods the patient uses from the system at their leisure. This system increases the number of therapeutic sessions a user can have per week. Additionally the reporting module within the system provides the therapist greater insight in the hills and troughs of emotional experience within the user's life which now is limited by what the patient journals remembers and self-reports to the therapist. Face to face therapeutic sessions become more meaningful as the system permits the therapist to focus on the emotional problems faced by the user during times the therapist is not present. The system tracks the user's emotional changes during the times they are not with a therapist and provide a report to the therapist. The therapists use the reporting module to identify hot spots in the user's day to day life situation and can focus their therapeutic sessions on what led up to any emotional crisis and even further diagnose the individual in ways they are unable to do sitting in an office during the 1 hour or 2 hour once a week isolated sessions.

Exemplary Operating Environment

Implementations of the invention include implementations as a computer system programmed to execute the method or methods described herein, and as a computer program product. According to the computer system implementations, sets of instructions for executing the method or methods may be resident in the memory of one or more computer systems configured generally as described above. Until required by processing system 10, the set of instructions may be stored as a computer program product in another computer memory, for example. Furthermore, the computer program product may also be stored at another computer and transmitted when desired to the user's workstation by a local area network or by an external communications network, such as the Internet or a wireless cellular network. One skilled in the art would appreciate that the physical storage of the sets of instructions physically changes the medium upon which it is stored so that the medium carries computer readable information. The change may be electrical, magnetic, chemical or some other physical change.

Although described in connection with an exemplary computing system environment, embodiments are operational with numerous other general purpose or special purpose computing system environments or configurations. The computer processing system environment is not intended to suggest any limitation as to the scope of use or functionality of any aspect. Moreover, the computing system environment should not be interpreted as having any dependency or requirement relating to any one or combination of components illustrated in the exemplary operating environment. Examples of well-known computing systems, environments, and/or configurations that may be suitable for use with aspects include, but are not limited to, personal computers, server computers, hand-held or laptop computing devices, multiprocessor systems, microprocessor-based systems, programmable consumer electronics, mobile telephones, network PCs, minicomputers, mainframe computers, distributed computing environments that include any of the above systems or devices, and the like.

Embodiments may be described in the general context of computer-executable instructions, such as program modules, executed by one or more computers or other devices. The computer-executable instructions may be organized into one or more computer-executable components or modules. Generally, program modules include, but are not limited to, routines, programs, objects, components, and data structures that perform particular tasks or implement particular abstract data types. Aspects may be implemented with any number and organization of such components or modules. For example, aspects are not limited to the specific computer-executable instructions or the specific components or modules illustrated in the figures and described herein. Other embodiments may include different computer-executable instructions or components having more or less functionality than illustrated and described herein. The order of execution or performance of the operations in embodiments illustrated and described herein is not essential, unless otherwise specified. That is, the operations may be performed in any order, unless otherwise specified, and embodiments may include additional or fewer operations than those disclosed herein. For example, it is contemplated that executing or performing a particular operation before, contemporaneously with, or after another operation is within the scope of aspects.

It is understood that the use of specific component, device and/or parameter names and/or corresponding acronyms thereof, such as those of the executing utility, logic, and/or firmware described herein, are for example only and not meant to imply any limitations on the described embodiments. The embodiments may thus be described with different nomenclature and/or terminology utilized to describe the components, devices, parameters, methods and/or functions herein, without limitation. References to any specific protocol or proprietary name in describing one or more elements, features or concepts of the embodiments are provided solely as examples of one implementation, and such references do not limit the extension of the claimed embodiments to embodiments in which different element, feature, protocol, or concept names are utilized. Thus, each term utilized herein is to be given its broadest interpretation given the context in which that term is utilized.

When introducing elements of aspects or the embodiments thereof, the articles "a," "an," "the," and "said" are intended to mean that there are one or more of the elements. The terms "comprising," "including," and "having" are intended to be inclusive and mean that there may be additional elements other than the listed elements. Having described aspects in detail, it will be apparent that modifications and variations are possible without departing from the scope of aspects as defined in the appended claims. As various changes could be made in the above constructions, products, and methods without departing from the scope of aspects, it is intended that all matter contained in the above description and shown in the accompanying drawings shall be interpreted as illustrative and not in a limiting sense.

Although the invention has been described with reference to specific embodiments, these descriptions are not meant to be construed in a limiting sense. Various modifications of the disclosed embodiments, as well as alternative embodiments of the invention will become apparent to persons skilled in the art upon reference to the description of the invention. It should be appreciated by those skilled in the art that the conception and the specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

It is therefore, contemplated that the claims will cover any such modifications or embodiments that fall within the true scope of the invention.

What is claimed is:

1. A computer-implemented method of assessing and improving a user's life skills and self-efficacy for life stage readiness, comprising:
    providing a life stage readiness application which includes:
        a life skills measurement module, and
        a reverse engineering diagnosis module;
    providing a plurality of databases including:
        a life skills baseline score database for storing a numeric scoring system for scoring life skill competencies, the scoring system including a baseline score for each of a plurality of preselected life skill competencies and a composite baseline score for the plurality of preselected life skill competencies for each of a plurality of preselected life stage transitions,
        a life skills measurement database for storing data about the user's symptoms and other evidence of the user's mental and emotional health and life skill competencies of the user, and
        a reverse engineering diagnoses database for storing data of a plurality of human syndromes and disorders and other evidence of a human's emotional and mental health associated with each of such syndromes and disorders;
    using the life skills measurement module, collecting from the user via a user access device over a communications network data about the user's symptoms and other evidence of the user's life skills and mental and emotional health and storing such collected data in the life skills measurement database;
    assessing the user's readiness for a life stage transition based upon the collected user symptoms and other evidence wherein such assessing includes, in at least one interactive session with the user via the user access device over the communications network, measuring a plurality of life skill competencies, wherein the measuring of a plurality of life skill competencies includes generating quantitative scores based upon the numeric scoring system of the user's self-image, self-management skills, risk/reward predisposition, interpersonal skills, and existence or non-existence of one or more syndromes and disorders;
    using the reverse engineering diagnosis module, generating a plurality of potential differential diagnoses by comparing the user's collected symptoms and other evidence of the user's mental and emotional health with the symptoms and other evidence of mental and emotional health associated with each of the plurality of human syndromes and disorders stored in the reverse engineering diagnoses database;
    ranking the plurality of potential diagnoses using the reverse engineering diagnosis module from most likely to least likely;
    wherein the assessing of the user's readiness for a life stage transition includes:
        determining a composite score of the scores of the measured life skill competencies; and comparing the composite score to the respective baseline composite score stored in the life skills baseline score database for the life stage transition, which baseline composite score is predictive of the user's readiness or unreadiness for success in the life stage transition;

upon determining that the user's measured composite score is greater than the baseline composite score, outputting to the user the measured composite score indicative of the user's readiness for the life stage transaction.

2. The method of claim 1, wherein:

the life stage readiness application further includes:
   a dynamic treatment module for executing a plurality of treatment programs for treating a plurality of mental and emotional syndromes and disorders; and
   a life skills training module for executing a plurality of training programs for improving a user's readiness for a life stage transition;

the plurality of databases further includes:
   a dynamic treatment database storing a plurality of treatment programs for treating a plurality of mental and emotional syndromes and disorders; and
   a life skills training database storing a plurality of training programs for improving a user's readiness for a life stage transition;

upon determining that the user's measured composite score is less than the baseline composite score, comparing the user's scores for each of the measured life skill competencies to the respective baseline score stored in the life skills baseline score database for each of the plurality of measured life skill competencies and determining whether the user has a deficit score associated with any of the plurality of measured life skill competencies;

outputting to the user access device the measured scores of the measured life skill competencies indicative of either a diagnosis of a syndrome or disorder or a life skill deficiency;

upon the generating of a diagnosis of a syndrome or disorder, selecting at least one treatment program from the plurality of treatment programs in the dynamic treatment database for providing treatment for the first most likely diagnosis;

using the selected at least one treatment program, interactively engaging in at least one session with the user over the communications network to improve the user's readiness for the life stage transition;

guiding the user to input a value rating of the at least one session of the at least one treatment program taken by the user;

upon the outputting of a diagnosis of a life skill deficiency, selecting at least one training program from the plurality of training programs in the life skills training database for providing training to improve the indicated life skill deficiency;

using the selected at least one training program, interactively engaging in at least one session with the user over the communications network to improve the user's readiness for the life stage transition;

guiding the user to input a value rating of the at least one session of the at least one training program taken by the user; and in response to the user's rating of either the at least one session of the at least one treatment program or the at least one session of the at least one training program, reassessing the user's most likely diagnosis from the plurality of differential diagnoses generated by said application and reassessing the user's readiness for the life stage transition.

3. The method of claim 1, wherein the individual baseline score for each of the plurality of life skill competencies and the composite baseline score for the plurality of life stage transitions are heuristically determined based upon aggregate scores gathered from all users of the method that report success for the particular life stage transition for which the baseline scores are determined.

4. The method of claim 1, wherein the step of ranking comprises:
   ranking and prioritizing the plurality of generated potential differential diagnoses by a plurality of inclusionary/inclusionary features wherein such features include the presence or absence of a traumatic event.

5. The method of claim 2, wherein the step of collecting from the user and storing in the life skills measurement database further comprises:
   collecting evidence of the user's personality in order to determine the user's personality type; and the method further comprises:
   upon the at least one treatment program being selected, customizing the at least one treatment program for the user's personality type developed from the collected evidence and
   upon the at least one training program being selected, customizing the at least one training program for the user's personality type developed from the collected evidence.

6. The method of claim 5, further comprising:
   assessing whether the at least one session of the at least one treatment program engaged by the user results in negative user emotions; and
   upon receiving feedback from the user of negative user emotions resulting from the user's engagement with the at least one treatment program, guiding the user to an emotional care program for overcoming or reducing the user's negative emotions.

7. The method of claim 6, further comprising:
   using the feedback received from the user to refine the selected at least one treatment program to improve the efficacy of future sessions of the refined at least one treatment program thereby dynamically customizing the user's treatment to the user's individual needs and personality.

8. The method of claim 5, further comprising:
   assessing whether the at least one session of the at least one treatment program engaged in by the user results in negative user emotions; and
   upon detecting negative user emotions, guiding the user to an emotion care module for evaluating the intensity of the user's negative emotions;
   upon the emotion care module receiving feedback from the user of high intensity negative emotions, directing the user to one of a plurality of virtual rooms having a plurality of simulations for overcoming or reducing the user's negative emotions wherein the virtual room to which the user is directed depends on the type of negative emotion detected;
   using the emotion care module, displaying the selected virtual room over the communications network within a graphical user interface on the screen of the user's access device to permit the user to interactively engage with the plurality of simulations contained in the selected virtual room environment to reduce the type of negative emotion detected.

9. The method of claim 8, further comprising:
if a second treatment program is selected, using the feedback from the user to refine the second treatment program to improve the efficacy of any future sessions of the refined second treatment program.

10. The method of claim 2, further comprising:
using a personality neutral and nonjudgmental avatar projected on the graphical user interface of the user's access device, making suggestions to the user to improve his life skill competencies for the particular life stage transition.

11. The method of claim 10, wherein the step of making suggestions further comprises:
guiding the user through a defined process that includes the creation of goals, tasks, and milestones.

12. The method of claim 11, wherein the step of guiding the user comprises:
periodically outputting reminders of goals, tasks, and milestones over a communications network to the user's personal digital assistant to reinforce the steps to be taken by the user to improve the user's life skill competencies for a particular life stage transition.

13. A system for assessing and improving a user's life skills and self-efficacy for life stage readiness, the computer system comprising:
at least one storage device for storing code data in a plurality of databases including:
a life skills baseline score database for storing a numeric scoring system for scoring life skill competencies, the scoring system including a baseline score for each of a plurality of preselected life skill competencies and a composite baseline score for the plurality of preselected life skill competencies for each of a plurality of preselected life stage transitions,
a life skills measurement database for storing data about the user's symptoms and other evidence of the user's mental and emotional health and life skill competencies of the user, and
a reverse engineering diagnoses database for storing data of a plurality of human syndromes and disorders and other evidence of a human's emotional and mental health associated with each of such syndromes and disorders; and
at least one processor in communication with the at least one storage device wherein the at least one storage device has stored thereon at least one program for controlling the processor for processing the code data to:
collect from the user via a user access device over a communications network and store in the life skills measurement database in communication with the processor code data about the user's symptoms and other evidence of the user's emotional and mental health and life skills;
assess the user's readiness for a life stage transition based upon the collected user symptoms and other evidence wherein such assessing includes, in at least one interactive session with the user via the user access device over the communications network, measuring a plurality of life skill competencies wherein the measuring of a plurality of life skill competencies includes generating quantitative scores based upon the numeric scoring system of the user's self-image, self-management skills, risk/reward predisposition, interpersonal skills, and existence or non-existence of one or more syndromes and disorders;
generate a plurality of potential differential diagnoses by comparing the user collected symptoms and other evidence of the user's mental and emotional health with the symptoms and other evidence of mental and emotional health associated with the human syndromes and disorders stored in the reverse engineering diagnosis database;
rank the plurality of potential diagnoses from most likely to least likely;
wherein the assessing of the user's readiness for a life stage transition includes:
determining a composite score of the scores of the measured life skill competencies; and
comparing the composite score to the respective baseline composite score stored in the life skills baseline score database for the life stage transition, which baseline composite score is predictive of the user's readiness or unreadiness for success in the life stage transition;
upon determining that the user's measured composite score is greater than the baseline composite score, output to the user the measured composite score indicative of the user's readiness for the life stage transaction.

14. The system of claim 13, wherein:
the plurality of databases further includes:
a dynamic treatment database storing a plurality of treatment programs for treating a plurality of mental and emotional syndromes and disorders; and
a life skills training database storing a plurality of training programs for improving a user's readiness for a life stage transition;
the at least one processor is further operative to execute the code data to:
upon determining that the user's measured composite score is less than the baseline composite score to compare the user's scores for each of the measured life skill competencies to the respective baseline score stored in the life skills baseline score database for each of the plurality of measured life skill competencies and determining whether the user has a deficit score associated with any of the plurality of measured life skill competencies;
output to the user access device the measured scores of the at least measured life skill competencies indicative of either a diagnosis of a syndrome or disorder or a life skill deficiency;
upon the generating of a diagnosis of a syndrome or disorder, select at least one treatment program from the plurality of treatment programs in the dynamic treatment database for providing treatment for the first most likely diagnosis;
using the selected at least one treatment program, interactively engage in at least one session with the user over the communications network to improve the user's readiness for the life stage transition;
guide the user to input a value rating of the at least one session of the at least one treatment program taken by the user;
upon the generating of a diagnosis of a life skill deficiency, select at least one training program from the plurality of training programs in the life skills training database for providing training to improve the indicated life skill deficiency;
using the selected at least one training program, interactively engage in at least one session with the user over the communications network to improve the user's readiness for the life stage transition;

guide the user to input a value rating of the at least one session of the at least one training program taken by the user; and
in response to the user's rating of either the at least one session of the at least one treatment program or the at least one session of the at least one training program, reassess the user's most likely diagnosis from the plurality of differential diagnoses generated by said application and reassess the user's readiness for the life stage transition.

15. The system of claim 14, wherein the individual baseline score for each of the plurality of life skill competencies and the composite baseline score for the plurality of life stage transitions are heuristically determined based upon aggregate scores gathered from all users of the method that report success for the particular life stage transition for which the baseline scores are determined.

16. The system of claim 13, wherein ranking comprises:
ranking and prioritizing the plurality of generated potential differential diagnoses by a plurality of inclusionary/inclusionary features wherein such features include the presence or absence of a traumatic event.

17. The system of claim 14, wherein:
collecting from the user and storing in the life skills database further comprises collecting evidence of the user's personality in order to determine the user's personality type; and
the at least one processor is further operative to execute the code data to:
customize, upon the at least one treatment program being selected, the at least one treatment program for the user's personality type developed from the collected evidence; and
customize, upon the at least one training program being selected, the at least one training program for the user's personality type developed from the collected evidence.

18. The system of claim 17, wherein the at least one processor is further operative to execute the code data to:
assess whether the at least one session of the at least one treatment program engaged by the user results in negative user emotions; and
upon receiving feedback from the user of negative user emotions resulting from the user's engagement with the at least one treatment program, guide the user to an emotional care program for overcoming or reducing the user's negative emotions.

19. The system of claim 18, wherein the at least one processor is further operative to execute the code data to:
use the feedback received from the user to refine the selected at least one treatment program to improve the efficacy of future sessions of the refined at least one treatment program thereby dynamically customizing the user's treatment to the user's individual needs and personality.

20. The system of claim 17, wherein the at least one processor is further operative to execute the code data to:
assess whether the at least one session of the at least one treatment program engaged by the user results in negative user emotions; and
upon detecting negative user emotions, evaluate the intensity of the user's negative emotions;
upon receiving feedback from the user of high intensity negative user emotions, direct the user to one of a plurality of virtual rooms having a plurality of simulations for overcoming or reducing the user's negative emotions wherein the virtual room to which the user is directed depends on the type of negative emotion detected;
display the selected virtual room over the communications network within a graphical user interface on a screen of the user's access device to permit the user to interactively engage with the plurality of simulations executed in the selected virtual room environment to reduce the type of negative emotion detected.

21. The system of claim 20, wherein the at least one processor is further operative to execute the code data to:
use, if a second treatment program is selected, the feedback from the user to refine the second treatment program to improve the efficacy of any future sessions of the refined second treatment program.

22. The system of claim 13, wherein the at least one processor is further operative to execute the code data to:
using a personality neutral and nonjudgmental avatar projected in a graphical user interface on the screen of the user's access device, make suggestions to the user to improve his life skill competencies for the particular life stage transition.

23. The system of claim 22, wherein making suggestions further comprises:
guiding the user through a defined process that includes the creation of goals, tasks, and milestones.

24. The system of claim 23, wherein the guiding the user comprises:
periodically outputting reminders of goals, tasks, and milestones over a communications network to the user's personal digital assistant to reinforce the steps to be taken by the user to improve the user's life skill competencies for a particular life stage transition.

25. A computer program code embodied in a computer-readable device for assessing and improving a user's life skills and self-efficacy for life stage readiness, the computer program code comprising processor executable instructions of a life stage readiness application which includes:
a life skills measurement module, and
a reverse engineering diagnosis module; and
a plurality of databases including:
a life skills baseline score database for storing a numeric scoring system for scoring life skill competencies, the scoring system including a baseline score for each of a plurality of preselected life skill competencies and a composite baseline score for the plurality of preselected life skill competencies for each of a plurality of preselected life stage transitions,
a life skills measurement database for storing data about the user's symptoms and other evidence of the user's mental and emotional health and life skill competencies of the user, and
a reverse engineering diagnoses database for storing data of a plurality of human syndromes and disorders and other evidence of a human's emotional and mental health associated with each of such syndromes and disorders;
for:
collecting from the user and storing in the life skills measurement database user symptoms and other evidence of the user's life skills and emotional and mental health;
assessing the user's readiness for a life stage transition based upon the collected user symptoms and other evidence wherein such assessing includes, in at least one interactive session with the user, measuring a plurality of life skill competencies wherein the measuring of a plurality of life skill competencies includes generating quantitative scores based upon the numeric scoring system of the user's self-image, self-management skills, risk/reward predisposition, interpersonal skills, and existence or non-existence of one or more syndromes and disorders;

generating a plurality of potential differential diagnoses by comparing the user's collected symptoms and other evidence of the user's mental and emotional health with the symptoms and other evidence of mental and emotional health associated with each of the plurality of human syndromes and disorders stored in the reverse engineering diagnoses database;

ranking the plurality of potential diagnoses from most likely to least likely;

wherein the assessing of the user's readiness for a life stage transition includes:
  determining a composite score of the scores of the measured life skill competencies; and
  comparing the composite score to the respective baseline composite score stored in the life skills baseline score database for the life stage transition, which baseline composite score is predictive of the user's readiness or unreadiness for success in the life stage transition;
  upon determining that the user's measured composite score is greater than the baseline composite score, outputting to the user the measured composite score indicative of the user's readiness for the life stage transaction.

26. The computer program code of claim 25, wherein:
the application further includes:
  a dynamic treatment module for executing a plurality of treatment programs for treating a plurality of mental and emotional syndromes and disorders; and
  a life skills training module for executing a plurality of training programs for improving a user's readiness for a life stage transition;
the plurality of databases further includes:
  a dynamic treatment database storing a plurality of treatment programs for treating a plurality of mental and emotional syndromes and disorders; and
  a life skills training database storing a plurality of training programs for improving a user's readiness for a life stage transition; and
upon determining that the user's measured composite score is less than the baseline composite score, comparing the user's scores for each of the measured life skill competencies to the respective baseline score stored in the life skills baseline score database for each of the plurality of measured life skill competencies and determining whether the user has a deficit score associated with any of the plurality of measured life skill competencies;
outputting to the user access device the measured scores of the at least measured life skill competencies indicative of either a diagnosis of a syndrome or disorder or a life skill deficiency;
upon the generating of a diagnosis of a syndrome or disorder, selecting at least one treatment program from the plurality of treatment programs in the dynamic treatment database for providing treatment for the first most likely diagnosis;
using the selected at least one treatment program, interactively engaging in at least one session with the user to improve the user's readiness for the life stage transition;
guiding the user to input a value rating of the at least one session of the at least one treatment program taken by the user;
upon the generating of a diagnosis of a life skill deficiency, selecting at least one training program from the plurality of training programs in the life skills training database for providing training to improve the indicated life skill deficiency;
using the selected at least one training program, interactively engaging in at least one session with the user over the communications network to improve the user's readiness for the life stage transition;
guiding the user to input a value rating of the at least one session of the at least one training program taken by the user; and
in response to the user's rating of either the at least one session of the at least one treatment program or the at least one session of the at least one training program, reassessing the user's most likely diagnosis from the plurality of differential diagnoses generated by said application and reassessing the user's readiness for the life stage transition.

27. The computer program code of claim 25, wherein the individual baseline score for each of the plurality of life skill competencies and the composite baseline score for the plurality of life stage transitions are heuristically determined based upon aggregate scores gathered from all users of the method that report success for the particular life stage transition for which the baseline scores are determined.

28. The computer program code of claim 25, wherein ranking comprises:
  ranking and prioritizing the plurality of generated potential differential diagnoses by a plurality of inclusionary/inclusionary features wherein such features include the presence or absence of a traumatic event.

29. The computer program code of claim 25, wherein collecting from the user and storing in the life skills measurement database further comprises:
  collecting evidence of the user's personality in order to determine the user's personality type; and the method further comprises:
  upon the at least one treatment program being selected, customizing the at least one treatment program for the user's personality type developed from the collected evidence; and
  upon the at least one training program being selected, customizing the at least one training program for the user's personality type developed from the collected evidence.

30. The computer program code of claim 29, wherein the computer program code executes processes executable instructions for:
  assessing whether the at least one session of the at least one treatment program engaged by the user results in negative user emotions; and
  upon receiving feedback from the user of negative user emotions resulting from the user's engagement with the at least one treatment program, guiding the user to an emotional care program for overcoming or reducing the user's negative emotions.

31. The computer program code of claim 30, wherein the computer program code executes processes executable instructions for:

using the feedback received from the user to refine the at least one treatment program to improve the efficacy of future sessions of the refined at least one treatment program thereby dynamically customizing the user's treatment to the user's individual needs and personality.

32. The computer program code of claim 31, wherein the computer program code executes processes executable instructions for:
assessing whether the at least one session of the at least one treatment program engaged in by the user results in negative user emotions; and
upon detecting negative user emotions, guiding the user to an emotion care module for evaluating the intensity of the user's negative emotions;
upon receiving feedback from the user of high intensity negative user emotions, directing the use to one of a plurality of virtual rooms having a plurality of simulations for overcoming or reducing the user's negative emotions wherein the virtual room to which the user is directed depends on the type of negative emotion detected; and
using the emotion care module, displaying the selected virtual room over the communications network within a graphical user interface on the screen of the user's access device to permit the user to interactively engage with the plurality of simulations contained in the selected virtual room environment to reduce the type of negative emotion detected.

33. The computer program code of claim 32, wherein the computer program code executes processes executable instructions for:
if a second treatment program is selected, using the feedback from the user to refine the second treatment program to improve the efficacy of any future sessions of the refined second treatment program.

34. The computer program code of claim 25, wherein the computer program code executes processes executable instructions for:
using a personality neutral and nonjudgmental avatar projected on the graphical user interface of the user's access device, making suggestions to the user to improve his life skill competencies for the particular life stage transition.

35. The computer program code of claim 25, wherein making suggestions further comprises:
guiding the user through a defined process that includes the creation of goals, tasks, and milestones.

36. The computer program code of claim 25, wherein guiding the user comprises:
periodically outputting reminders of goals, tasks, and milestones to the user's personal digital assistant to reinforce the steps to be taken by the user to improve the user's life skill competencies for a particular life stage transition.

* * * * *